(12) United States Patent
Ogura

(10) Patent No.: US 6,835,946 B2
(45) Date of Patent: Dec. 28, 2004

(54) IMAGE READING METHOD AND APPARATUS

(75) Inventor: Nobuhiko Ogura, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 428 days.

(21) Appl. No.: 09/996,672

(22) Filed: Nov. 30, 2001

(65) Prior Publication Data
US 2002/0066866 A1 Jun. 6, 2002

(30) Foreign Application Priority Data
Dec. 4, 2000 (JP) ........................................ 2000-368112

(51) Int. Cl.$^7$ .......................... G21N 21/64; G03B 42/02
(52) U.S. Cl. .................. 250/584; 250/461.2; 250/458.1
(58) Field of Search ................................. 250/584, 585, 250/586, 591, 583, 488.1, 580, 581, 458.1, 459.1, 461.1, 461.2, 484.2, 484.4, 486.4

(56) References Cited

U.S. PATENT DOCUMENTS

| | | | |
|---|---|---|---|
| 3,859,527 A | * | 1/1975 | Luckey ....................... 250/581 |
| 4,877,965 A | * | 10/1989 | Dandliker et al. ........ 250/458.1 |
| 4,880,987 A | * | 11/1989 | Hosoi et al. ............. 250/484.4 |
| 4,922,103 A | * | 5/1990 | Kawajiri et al. ............ 250/586 |
| 5,270,162 A | * | 12/1993 | Shiraishi et al. ............... 435/6 |
| 5,900,640 A | * | 5/1999 | Ogura ......................... 250/583 |
| 6,326,636 B1 | * | 12/2001 | Isoda et al. .................. 250/586 |
| 6,369,402 B1 | * | 4/2002 | Gebele et al. .............. 250/585 |
| 6,373,074 B1 | * | 4/2002 | Mueller et al. ............. 250/584 |

* cited by examiner

Primary Examiner—Albert Gagliardi
(74) Attorney, Agent, or Firm—Sughrue Mion, PLLC

(57) ABSTRACT

An image reading apparatus is adapted for irradiating an image carrier including a labeling substance contained in two-dimensionally distributed spots with a stimulating ray and photoelectrically detecting light released from the labeling substance, thereby producing image data, and the image reading apparatus includes at least one stimulating ray source for emitting a stimulating ray, a lens for shaping the stimulating ray emitted from the at least one stimulating ray source into a line beam, a sensor for photoelectrically detecting light released from the labeling substance, and a controller for performing a stimulation and detection step of irradiating the image carrier including the labeling substance contained in the two-dimensionally distributed spots with the line beam of the stimulating ray to stimulate the labeling substance, stopping irradiation with the line beam of the stimulating ray and causing the sensor to photoelectrically detect light released from the labeling substance after the completion of irradiation with the line beam of the stimulating ray. According to the thus constituted image reading apparatus, it is possible to produce low noise image data rapidly and with a simple operation by irradiating an image carrier including two-dimensionally distributed spots of a labeling substance such as a fluorescent substance, a radioactive labeling substance or the like with a stimulating ray to excite the labeling substance and photoelectrically detecting light released from the labeling substance.

41 Claims, 11 Drawing Sheets

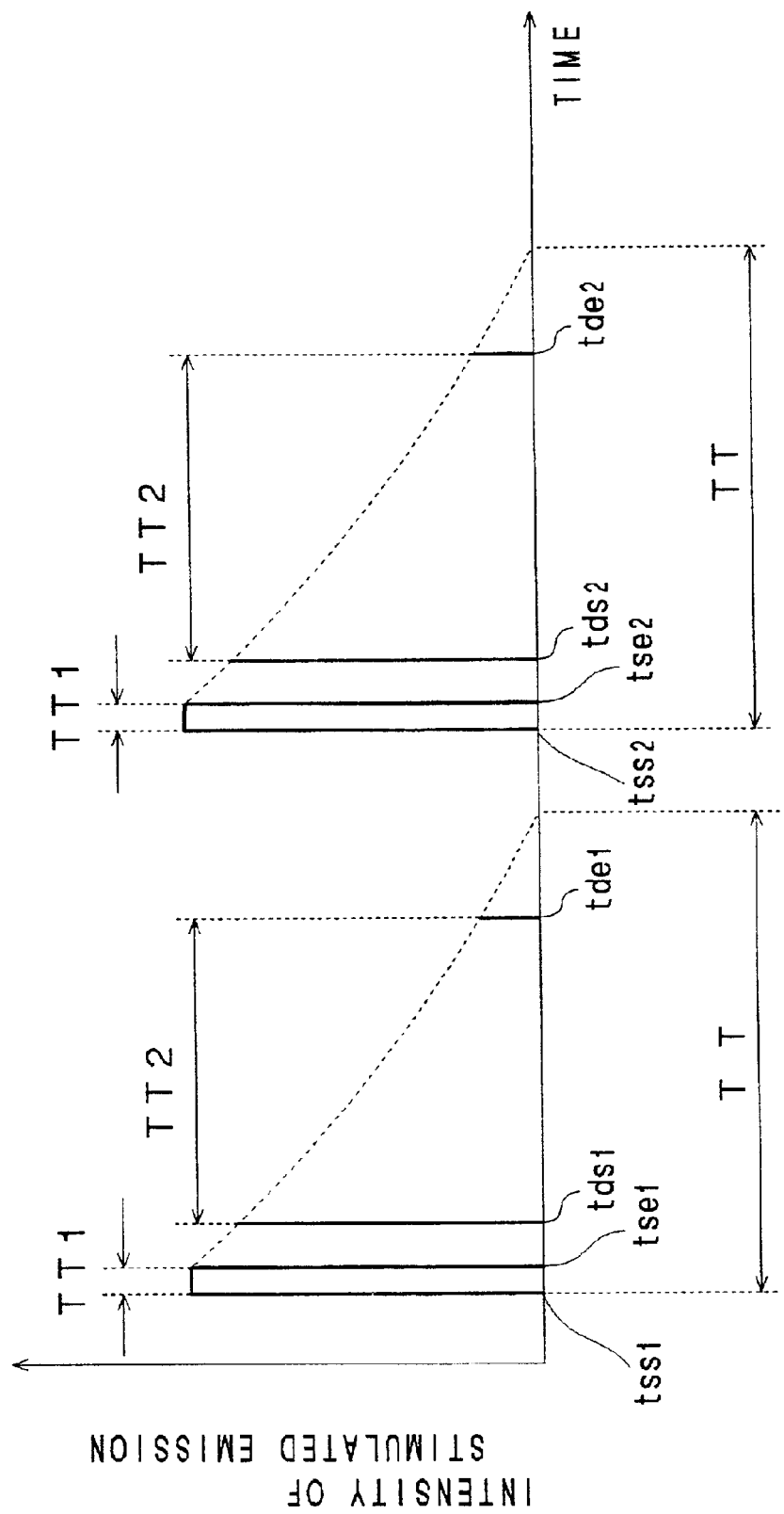

IMAGE READING METHOD AND APPARATUS

BACKGROUND OF THE INVENTION

The present invention relates to an image reading method and apparatus and, particularly, to an image reading method and apparatus which can produce low noise image data rapidly and with a simple operation by irradiating an image carrier including two-dimensionally distributed spots of a labeling substance such as a fluorescent substance, a radioactive labeling substance or the like with a stimulating ray to excite the labeling substance and photoelectrically detecting light released from the labeling substance.

DESCRIPTION OF THE PRIOR ART

There is known a radiation diagnosis system comprising the steps of employing, as a detecting material for the radiation, a stimulable phosphor which can absorb and store the energy of radiation upon being irradiated therewith and release a stimulated emission whose amount is proportional to that of the received radiation upon being stimulated with an electromagnetic wave having a specific wavelength range, storing and recording the energy of radiation transmitted through an object in the stimulable phosphor contained in a stimulable phosphor layer formed on a stimulable phosphor sheet, scanning the stimulable phosphor layer with an electromagnetic wave to excite the stimulable phosphor, photoelectrically detecting the stimulated emission released from the stimulable phosphor to produce digital image signals, effecting image processing on the obtained digital image signals, and reproducing an image on displaying means such as a CRT or the like or a photographic film (see, for example, Japanese Patent Application Laid Open Nos. 55-12429, 55-116340, 55-163472, 56-11395, 56-104645 and the like).

There is also known an autoradiography detection system comprising the steps of employing a similar stimulable phosphor as a detecting material for the radiation, introducing a radioactive labeling substance into an organism, using the organism or a part of the tissue of the organism as a specimen, placing the specimen and a stimulable phosphor sheet formed with a stimulable phosphor layer together in layers for a certain period of time, storing and recording radiation energy in a stimulable phosphor contained in the stimulable phosphor layer, scanning the stimulable phosphor layer with an electromagnetic wave to excite the stimulable phosphor, photoelectrically detecting the stimulated emission released from the stimulable phosphor to produce digital image signals, effecting image processing on the obtained digital image signals, and reproducing an image on displaying means such as a CRT or the like or a photographic film (see, for example, Japanese Patent Publication No. 1-60784, Japanese Patent Publication No. 1-60782, Japanese Patent Publication No. 4-3952 and the like).

There is further known a chemiluminescence detection system using as a detecting material for detecting light a stimulable phosphor which can absorb, store and record the light energy when it is irradiated with light and which, when it is then stimulated by an electromagnetic wave having a specified wavelength, can release stimulated emission whose light amount corresponds to the amount of light radiation with which it was irradiated, which comprises the steps of selectively labeling a fixed high molecular substance such as a protein or a nucleic acid sequence with a labeling substance which generates chemiluminescent emission when it contacts a chemiluminescent substance, contacting the high molecular substance selectively labeled with the labeling substance and the chemiluminescent substance, photoelectrically detecting the chemiluminescent emission in the wavelength of visible light generated by the contact of the chemiluminescent substance and the labeling substance and producing digital image signals, effecting image processing thereon, and reproducing a chemiluminescent image on a display means such as a CRT or a recording material such as a photographic film, thereby obtaining information relating to the high molecular substance such as genetic information (see, for example, U.S. Pat. No. 5,028,793, British Patent Publication GB No. 2,246,197A and the like).

There are further known an electron microscopic detection system and a radiographic diffraction image detection system comprising the steps of employing, as a detecting material for an electron beam or radiation, a stimulable phosphor which can absorb and store the energy of an electron beam or radiation upon being irradiated therewith and release a stimulated emission whose amount is proportional to that of the received electron beam or radiation upon being stimulated with an electromagnetic wave having a specific wavelength range, irradiating a metal or nonmetal specimen with an electron beam and effecting elemental analysis, composition analysis or structural analysis of the specimen by detecting a diffraction image or a transmission image, or irradiating the tissue of an organism with an electron beam and detecting an image of the tissue of the organism, or irradiating a specimen with radiation, detecting a radiographic diffraction image and effecting structural analysis of the specimen (see, for example, Japanese Patent Application Laid Open No. 61-51738, Japanese Patent Application Laid Open No. 61-93538, Japanese Patent Application Laid Open No. 59-15843 and the like).

Unlike a system using a photographic film, according to these systems using the stimulable phosphor as a detecting material for an image, development, which is chemical processing, becomes unnecessary. Further, it is possible reproduce a desired image by effecting image processing on the obtained image data and effect quantitative analysis using a computer. Use of a stimulable phosphor in these processes is therefore advantageous.

On the other hand, a fluorescence detecting system using a fluorescent substance as a labeling substance instead of a radioactive labeling substance in the autoradiographic system is known. According to this system, it is possible by reading a fluorescent image to study a genetic sequence, to study the expression level of a gene, and to effect separation or identification of protein or estimation of the molecular weight or properties of protein or the like. For example, this system can perform a process including the steps of distributing a plurality of DNA fragments on a gel support by means of electrophoresis after a fluorescent dye was added to a solution containing a plurality of DNA fragments to be distributed, or distributing a plurality of DNA fragments on a gel support containing a fluorescent dye, or dipping a gel support on which a plurality of DNA fragments have been distributed by means of electrophoresis in a solution containing a fluorescent dye, thereby labeling the electrophoresed DNA fragments, exciting the fluorescent dye by a stimulating ray to cause it to release fluorescent light, detecting the released fluorescent light to produce an image and detecting the distribution of the DNA fragments on the gel support. This system can also perform a process including the steps of distributing a plurality of DNA fragments on a gel support by means of electrophoresis, denaturing the DNA fragments, transferring at least a part of the denatured DNA fragments onto a transfer support such as a nitrocellulose support by the Southern-blotting method, hybridizing a probe prepared by labeling target DNA and DNA or RNA complementary thereto with the denatured DNA fragments, thereby selectively labeling only the DNA fragments complementary to the probe DNA or probe RNA, exciting the fluorescent dye by a stimulating ray to cause it to release fluorescent light, detecting the released fluorescent light to produce an image and detecting the distribution of the target DNA on the transfer support. This system can further perform a process including the steps of preparing a DNA probe complementary to DNA containing a target gene labeled by a labeling substance, hybridizing it with DNA on a transfer support, combining an enzyme with the complementary DNA labeled by a labeling substance, causing the enzyme to contact a fluorescent substance, transforming the fluorescent substance to a fluorescent substance having fluorescent light releasing property, exciting the thus produced fluorescent substance by a stimulating ray to release fluorescent light, detecting the fluorescent light to produce an image and detecting the distribution of the target DNA on the transfer support. This fluorescence detecting system is advantageous in that a genetic sequence or the like can be easily detected without using a radioactive substance.

Further, a micro-array detecting system has been recently developed, which comprises the steps of using a spotting device to drop at different positions on the surface of a carrier such as a slide glass plate, a transfer support filter, a gel support or the like specific binding substances, which can specifically bind with a substance derived from a living organism such as a hormone, tumor marker, enzyme, antibody, antigen, abzyme, other protein, a nuclear acid, cDNA, DNA, RNA or the like and whose sequence, base length, composition and the like are known, thereby forming a number of independent spots, specifically binding the specific binding substances using a hybridization method or the like with a substance derived from a living organism such as a hormone, tumor marker, enzyme, antibody, antigen, abzyme, other protein, a nuclear acid, cDNA, DNA or mRNA, which is gathered from a living organism by extraction, isolation or the like or is further subjected to chemical processing, chemical modification or the like and which is labeled with a labeling substance such as a fluorescent substance, dye or the like, thereby forming a micro-array, irradiating the micro-array with a stimulating ray, photoelectrically detecting light such as fluorescence emission released from a labeling substance such as a fluorescent substance, dye or the like, and analyzing the substance derived from a living organism. This micro-array image detecting system is advantageous in that a substance derived from a living organism can be analyzed in a short time period by forming a number of spots of specific binding substances at different positions of the surface of a carrier such as a slide glass plate at high density and hybridizing them with a substance derived from a living organism and labeled with a labeling substance.

In addition, a macro-array detecting system using a radioactive labeling substance as a labeling substance has been further developed, which comprises the steps of using a spotting device to drop at different positions on the surface of a carrier such as a membrane filter or the like specific binding substances, which can specifically bind with a substance derived from a living organism such as a hormone, tumor marker, enzyme, antibody, antigen, abzyme, other protein, a nuclear acid, cDNA, DNA, RNA or the like and whose sequence, base length, composition and the like are known, thereby forming a number of independent spots, specifically binding the specific binding substance using a hybridization method or the like with a substance derived from a living organism such as a hormone, tumor marker, enzyme, antibody, antigen, abzyme, other protein, a nuclear acid, cDNA, DNA or mRNA, which is gathered from a living organism by extraction, isolation or the like or is further subjected to chemical processing, chemical modification or the like and which is labeled with a radioactive labeling substance, thereby forming a macro-array, superposing the macro-array and a stimulable phosphor sheet formed with a stimulable phosphor layer, exposing the stimulable phosphor layer to a radioactive labeling substance, irradiating the stimulable phosphor layer with a stimulating ray to excite the stimulable phosphor, photoelectrically detecting the stimulated emission released from the stimulable phosphor to produce biochemical analysis data, and analyzing the substance derived from a living organism.

In the radiation diagnosis system, the autoradiography detection system, the chemiluminescence detection system, the electron microscopic detection system, the radiographic diffraction image detection system, the fluorescence detecting system, the micro-array detecting system and the macro-array detecting system, data for biochemical analysis such as image data are produced by irradiating a labeling substance with a stimulating ray to excite it and photoelectrically detecting stimulated emission or fluorescence emission released from the labeling substance by a light detector. Therefore, since noise is generated to lower the accuracy of analysis if the stimulating ray enters the light detector, a stimulating ray cut filter is provided for blocking the stimulating ray and preventing it from entering the light detector.

However, even when a stimulating ray cut filter is provided, it is difficult to completely block the stimulating ray. A method has been proposed for lowering noise caused by detecting the stimulating ray by stopping the irradiation with the stimulating ray after irradiating a labeling substance with the stimulating ray to excite the labeling substance and detecting residual stimulated emission or residual fluorescence emission released from the labeling substance even after the completion of the irradiation with the stimulating ray.

Image reading apparatuses used for these systems are classified into ones utilizing a scanner and ones utilizing a two-dimensional sensor. An image reading apparatus using a scanner is more advantageous than an image reading apparatus using a two-dimensional sensor in that data can be produced with a high resolution.

However, in the case where an image is read out using a scanner by irradiating two-dimensionally distributed spots of a labeling substance with a stimulating ray and detecting residual stimulated emission or residual fluorescence emission released from the labeling substance, since the amount of residual stimulated emission or residual fluorescence emission detected by one-time irradiation with the stimulating ray is small, it is necessary to repeat an operation comprising the steps of irradiation with the stimulating ray, stopping the irradiation with the stimulating ray and detecting residual stimulated emission or residual fluorescence emission. Therefore, it inevitably takes a long time.

Particularly, in the case where residual fluorescence emission is detected using a scanner by stimulating a fluorescent substance contained in a specimen solution held in a number of wells of a micro-titer plate, since the reaction of the specimen solution in the wells progresses with the elapse of time, unless a fluorescent substance contained in a specimen solution held in a well is stimulated and residual fluorescence emission released from a fluorescent substance is detected each time the specimen solution is poured into the well, residual fluorescence emission released from the specimen in the wells cannot be detected under the same condition. Therefore, it is not only time-consuming to detect residual fluorescence emission released from the specimen in the wells but also the operation is troublesome.

SUMMARY OF THE INVENTION

It is therefore an object of the present invention to provide an image reading method and apparatus which can produce low noise image data rapidly and with a simple operation by irradiating an image carrier including two-dimensionally distributed spots of a labeling substance such as a fluorescent substance, a radioactive labeling substance or the like with a stimulating ray to excite the labeling substance and photoelectrically detecting light released from the labeling substance.

The above and other objects of the present invention can be accomplished by an image reading method for producing image data by irradiating an image carrier including two-dimensionally distributed spots of a labeling substance with a stimulating ray to excite the labeling substance and photoelectrically detecting light released from the labeling substance, the image reading method further comprising a stimulation and detection step of irradiating the image carrier with a line beam of the stimulating ray to excite the labeling substance and photoelectrically detecting light released from the labeling substance after the completion of irradiation with the stimulating ray.

According to the present invention, although a labeling substance contained in two-dimensionally distributed spots is stimulated by irradiating an image carrier with the line beam of the stimulating ray, since light released from the labeling substance after the completion of irradiation with the stimulating ray is photoelectrically detected and light released from the labeling substance during irradiation with the line beam of the stimulating ray is not detected, it is possible to prevent noise caused by photoelectrically detecting the stimulating ray from being generated in image data produced by photoelectrically detecting light released from the labeling substance and to improve an S/N ratio.

Further, according to the present invention, since the labeling substance contained in two-dimensionally distributed spots is simultaneously stimulated by linearly irradiating an image carrier with the line beam of the stimulating ray, it is possible to rapidly produce image data by photoelectrically detecting light released from the labeling substance after the completion of irradiation with the line beam of the stimulating ray and even if the step of irradiation with the line beam of the stimulating ray and detection of light released from the labeling substance is repeated in order to increase an amount of light released from the labeling substance after the completion of irradiation with the line beam of the stimulating ray. Therefore, it is possible to rapidly produce image data in which noise caused by photoelectrically detecting the stimulating ray is lowered and which have a high S/N ratio.

Furthermore, according to the present invention, even in the case where a fluorescent substance contained in a specimen solution held in numerous wells of a micro-titer plate is to be stimulated, whereby residual fluorescence emission is to be detected, the specimen in the wells can be rapidly detected under the same condition without a complicated operation by pouring the specimen solution into the wells linearly formed in the micro-titer plate, stimulating the fluorescent substance contained in the specimen solution held in the wells and detecting residual fluorescence emission released from the fluorescent substance.

In a preferred aspect of the present invention, the image carrier is intermittently moved relative to the line beam of the stimulating ray in a direction perpendicular to a longitudinal direction of the line beam and the stimulation and detection step is performed each time the image carrier is moved, thereby scanning the whole surface of the image carrier with the line beam of the stimulating ray and image data are produced by photoelectrically detecting light released from the labeling substance contained in the spots two-dimensionally distributed in the image carrier.

According to this preferred aspect of the present invention, it is possible to rapidly read an image of the labeling substance carried in the image carrier and produce image data having a high S/N ratio while preventing noise caused by photoelectrically detecting the stimulating ray from being generated by irradiating the image carrier including the labeling substance contained in the two-dimensionally distributed spots with the line beam of the stimulating ray, intermittently moving the image carrier relative to the line beam of the stimulating ray in the direction perpendicular to the longitudinal direction of the line beam and photoelectrically detecting light released from the labeling substance after the completion of irradiation with the line beam of the stimulating ray.

In a further preferred aspect of the present invention, image data are produced by repeating the stimulation and detection step two or more times.

According to this preferred aspect of the present invention, since the image data are produced by repeating two or more times the stimulation and detection step of irradiating the image carrier with the line beam of the stimulating ray to excite the labeling substance and photoelectrically detecting light released from the labeling substance after the completion of irradiation with the line beam of the stimulating ray, an amount of light released from the labeling substance after the completion of irradiation with the line beam of the stimulating ray and to be detected can be increased, thereby producing image data having a high resolution.

In a further preferred aspect of the present invention, image data are produced by emitting the line beam of the stimulating ray from a laser diode or a laser diode array constituted by two or more laser diodes.

In another preferred aspect of the present invention, image data are produced by shaping a laser beam emitted from a laser stimulating ray source using a lens, thereby generating the line beam of the stimulating ray.

In another preferred aspect of the present invention, image data are produced by emitting the line beam of the stimulating ray from an LED array constituted by one or more LEDs.

In another preferred aspect of the present invention, image data are produced by shaping a stimulating ray emitted from an LED stimulating ray source using a lens, thereby generating the line beam of the stimulating ray.

In another preferred aspect of the present invention, image data are produced by shaping a stimulating ray emitted from a stimulating ray source using a slit, thereby generating the line beam of the stimulating ray.

In a further preferred aspect of the present invention, image data are produced by photoelectrically detecting light released from the labeling substance using a solid state imaging device.

In a further preferred aspect of the present invention, image data are produced by photoelectrically detecting light released from the labeling substance using a CCD line sensor.

In a further preferred aspect of the present invention, image data are produced by photoelectrically detecting light released from the labeling substance using a cooled CCD line sensor.

In a further preferred aspect of the present invention, image data are produced by photoelectrically detecting light released from the labeling substance using a photodiode array.

In a further preferred aspect of the present invention, image data are produced by photoelectrically detecting light released from the labeling substance using a cooled photodiode array.

In a further preferred aspect of the present invention, image data are produced by photoelectrically detecting light released from the labeling substance using a MOS type imaging device.

In a further preferred aspect of the present invention, image data are produced by photoelectrically detecting light released from the labeling substance using a cooled MOS type imaging device.

In a preferred aspect of the present invention, the labeling substance is formed of a fluorescent substance.

According to this preferred aspect of the present invention, since the image carrier including the fluorescent substance contained in two-dimensionally distributed spots is linearly irradiated with the line beam of the stimulating ray, thereby simultaneously stimulating the fluorescent substance in the respective spots, it is possible to rapidly produce image data by photoelectrically detecting residual fluorescence emission released from the fluorescent substance after the completion of irradiation with the line beam of the stimulating ray and even if the step of irradiation with the line beam of the stimulating ray and detection of light released from the fluorescent substance is repeated in order to increase an amount of residual fluorescence emission released from the fluorescent substance after the completion of irradiation with the line beam of the stimulating ray. Therefore, it is possible to rapidly produce image data in which noise caused by photoelectrically detecting the stimulating ray is lowered and which have a high S/N ratio.

In a further preferred aspect of the present invention, the image carrier is constituted as a membrane filter including the fluorescent substance contained in two-dimensionally distributed spots.

In a further preferred aspect of the present invention, the image carrier is constituted as a gel support including the fluorescent substance contained in two-dimensionally distributed spots.

In a further preferred aspect of the present invention, the image carrier is constituted as a micro-array including the fluorescent substance contained in two-dimensionally distributed spots.

In another preferred aspect of the present invention, the image carrier is constituted as a stimulable phosphor sheet formed with a stimulable phosphor layer including a radioactive labeling substance contained in two-dimensionally distributed spots.

According to this preferred aspect of the present invention, since the stimulable phosphor sheet formed with the stimulable phosphor layer including the radioactive labeling substance contained in two-dimensionally distributed spots is linearly irradiated with the line beam of the stimulating ray, thereby simultaneously exciting the radioactive labeling substance contained in the respective spots, it is possible to rapidly produce image data by photoelectrically detecting residual stimulated emission released from a stimulable phosphor after the completion of irradiation with the line beam of the stimulating ray and even if the step of irradiation with the line beam of the stimulating ray and detection of light released from the stimulable phosphor is repeated in order to increase an amount of residual stimulated emission released from the stimulable phosphor after the completion of irradiation with the line beam of the stimulating ray, it is still possible to rapidly produce image data in which noise caused by photoelectrically detecting the stimulating ray is lowered and which have a high S/N ratio.

The above and other objects of the present invention can be also accomplished by an image reading apparatus adapted for irradiating an image carrier including a labeling substance contained in two-dimensionally distributed spots with a stimulating ray and photoelectrically detecting light released from the labeling substance, thereby producing image data, the image reading apparatus comprising at least one stimulating ray source for emitting a stimulating ray, a stimulating ray shaping means for shaping the stimulating ray emitted from the at least one stimulating ray source into a line beam, a sensor for photoelectrically detecting light released from the labeling substance, and a control means for performing a stimulation and detection step of irradiating the image carrier including the labeling substance contained in the two-dimensionally distributed spots with the line beam of the stimulating ray to stimulate the labeling substance, stopping irradiation with the line beam of the stimulating ray and causing the sensor to photoelectrically detect light released from the labeling substance after the completion of irradiation with the line beam of the stimulating ray.

According to the present invention, although the image carrier is linearly irradiated with the stimulating ray emitted from the at least one stimulating ray source and shaped into a line beam to stimulate the labeling substance contained in the two-dimensionally distributed spots, since the sensor is constituted so as to photoelectrically detect light released from the labeling substance after the completion of irradiation with the line beam of the stimulating ray and not to detect light released from the labeling substance during irradiation with the line beam of the stimulating ray, it is possible to prevent noise caused by photoelectrically detecting the stimulating ray from being generated in image data produced by photoelectrically detecting light released from the labeling substance and to improve an S/N ratio.

Further, according to the present invention, since the image carrier is linearly irradiated with the stimulating ray emitted from the at least one stimulating ray source and shaped into a line beam to simultaneously stimulate the labeling substance contained in the two-dimensionally distributed spots, it is possible to rapidly produce image data by photoelectrically detecting light released from the labeling substance after the completion of irradiation with the line beam of the stimulating ray by the sensor and even if the step of irradiation with the line beam of the stimulating ray and detection of light released from the labeling substance is repeated in order to increase an amount of light released from the labeling substance after the completion of irradiation with the line beam of the stimulating ray. Therefore, it is possible to rapidly produce image data in which noise caused by photoelectrically detecting the stimulating ray is lowered and which have a high S/N ratio.

Furthermore, according to the present invention, even in the case where a fluorescent substance contained in a specimen solution held in numerous wells of a micro-titer plate is to be stimulated, whereby residual fluorescence emission is to be detected, the specimen in the wells can be rapidly detected under the same condition without a complicated operation by pouring the specimen solution into the wells linearly formed in the micro-titer plate, stimulating the fluorescent substance contained in a specimen solution held in the wells and detecting residual fluorescence emission released from the fluorescent substance.

In a preferred aspect of the present invention, the image reading apparatus further comprises a scanning means for intermittently moving the image carrier relative to the line beam of the stimulating ray in a direction perpendicular to a longitudinal direction of the line beam and the control means is constituted so as to perform the stimulation and detection step each time the image carrier is intermittently moved by the scanning means, thereby scanning a whole surface of the image carrier with the line beam of the stimulating ray and the sensor is constituted so as to photoelectrically detect light released from the labeling substance contained in the spots two-dimensionally distributed in the image carrier to produce image data.

According to this preferred aspect of the present invention, since the image reading apparatus further comprises a scanning means for intermittently moving the image carrier relative to the line beam of the stimulating ray in a direction perpendicular to a longitudinal direction of the line beam and the control means is constituted so as to perform the stimulation and detection step each time the image carrier is intermittently moved by the scanning means, thereby scanning a whole surface of the image carrier with the line beam of the stimulating ray and the sensor is constituted so as to photoelectrically detect light released from the labeling substance contained in the spots two-dimensionally distributed in the image carrier to produce image data, it is possible to rapidly read an image of the labeling substance carried in the image carrier and produce image data having a high SIN ratio while preventing noise caused by photoelectrically detecting the stimulating ray from being generated.

In a further preferred aspect of the present invention, the control means is constituted so as to repeat the stimulation and detection step two or more times.

According to this preferred aspect of the present invention, since the control means is constituted so as to repeat two or more times the stimulation and detection step of irradiating the image carrier with the line beam of the stimulating ray to excite the labeling substance and photoelectrically detecting light released from the labeling substance after the completion of irradiation with the stimulating ray, an amount of light released from the labeling substance after the completion of irradiation with the line beam of the stimulating ray and to be detected can be increased, thereby producing image data having a high resolution.

In a further preferred aspect of the present invention, the at least one stimulating ray source and the stimulating ray shaping means are constituted as a laser diode array provided with one or more laser diodes.

In a further preferred aspect of the present invention, the at least one stimulating ray source is constituted as a laser stimulating ray source and the stimulating ray shaping means is constituted as a lens.

In a further preferred aspect of the present invention, the at least one stimulating ray source and the stimulating ray shaping means are constituted as an LED array provided with one or more LEDs.

In a further preferred aspect of the present invention, the at least one stimulating ray source is constituted as an LED stimulating ray source and the stimulating ray shaping means is constituted as a lens.

In a further preferred aspect of the present invention, the stimulating ray shaping means is constituted as a slit.

In a further preferred aspect of the present invention, the sensor is constituted as a solid state imaging device.

In a further preferred aspect of the present invention, the sensor is constituted as a CCD line sensor.

In a further preferred aspect of the present invention, the sensor is constituted as a cooled CCD line sensor.

In a further preferred aspect of the present invention, the sensor is constituted as a photodiode array.

In a further preferred aspect of the present invention, the sensor is constituted as a cooled photodiode array.

In a further preferred aspect of the present invention, the sensor is constituted as a MOS type imaging device.

In a further preferred aspect of the present invention, the sensor is constituted as a cooled MOS type imaging device.

In a further preferred aspect of the present invention, the image reading apparatus further comprises a stimulating ray cut filter disposed in a path of light released from the labeling substance for cutting at least a light component having a wavelength of the stimulating ray.

According to this preferred aspect of the present invention, since the image reading apparatus further comprises a stimulating ray cut filter disposed in a path of light released from the labeling substance for cutting at least a light component having a wavelength of the stimulating ray, it is possible to more reliably prevent the sensor from photoelectrically detecting the stimulating ray and the S/N ratio of image data can be more markedly increased.

In a preferred aspect of the present invention, the labeling substance is formed of a fluorescent substance.

According to this preferred aspect of the present invention, since the image carrier including the fluorescent substance contained in two-dimensionally distributed spots is linearly irradiated with the line beam of the stimulating ray, thereby simultaneously stimulating the fluorescent substance in the respective spots, it is possible to rapidly produce image data by photoelectrically detecting residual fluorescence emission released from the fluorescent substance after the completion of irradiation with the line beam of the stimulating ray and even if the step of irradiation with the line beam of the stimulating ray and detection of light released from the fluorescent substance is repeated in order to increase an amount of residual fluorescence emission released from the fluorescent substance after the completion of irradiation with the line beam of the stimulating ray, it is still possible to rapidly produce image data in which noise caused by photoelectrically detecting the stimulating ray is lowered and which have a high S/N ratio.

In a further preferred aspect of the present invention, the image carrier is constituted as a membrane filter including the fluorescent substance contained in two-dimensionally distributed spots.

In a further preferred aspect of the present invention, the image carrier is constituted as a gel support including the fluorescent substance contained in two-dimensionally distributed spots.

In a further preferred aspect of the present invention, the image carrier is constituted as a micro-array including the fluorescent substance contained in two-dimensionally distributed spots.

In another preferred aspect of the present invention, the image carrier is constituted as a stimulable phosphor sheet formed with a stimulable phosphor layer including a radioactive labeling substance contained in two-dimensionally distributed spots.

According to this preferred aspect of the present invention, since the stimulable phosphor sheet formed with the stimulable phosphor layer including the radioactive labeling substance contained in two-dimensionally distributed spots is linearly irradiated with the line beam of the stimulating ray, thereby simultaneously exciting the radioactive labeling substance contained in the respective spots, it is possible to rapidly produce image data by photoelectrically detecting residual stimulated emission released from a stimulable phosphor after the completion of irradiation with the line beam of the stimulating ray and even if the step of irradiation with the line beam of the stimulating ray and detection of light released from the stimulable phosphor is repeated in order to increase an amount of residual stimulated emission released from the stimulable phosphor after the completion of irradiation with the line beam of the stimulating ray, it is still possible to rapidly produce image data in which noise caused by photoelectrically detecting the stimulating ray is lowered and which have a high S/N ratio.

The above and other objects and features of the present invention will become apparent from the following description made with reference to the accompanying drawings.

BRIEF DESCRIPTION OF THE DRAWINGS

FIG. 13 is a graph showing the relationship between irradiation time with a laser beam and the intensity of stimulated emission released from a stimulable phosphor.

DESCRIPTION OF THE PREFERRED EMBODIMENTS

Figure 1:
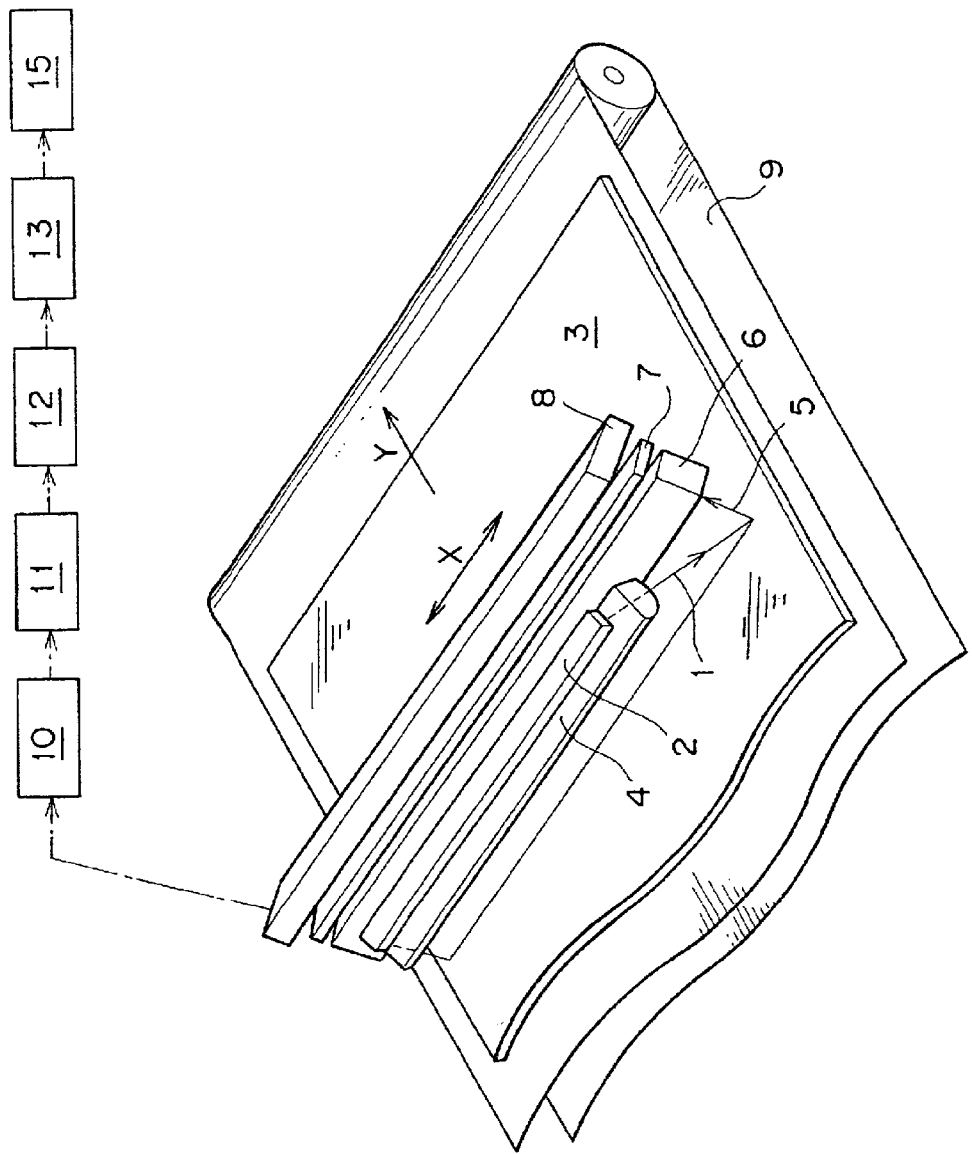
FIG. 1 is a schematic perspective view showing a fluorescent image reading apparatus which is a preferred embodiment of the present invention.
Figure 2:
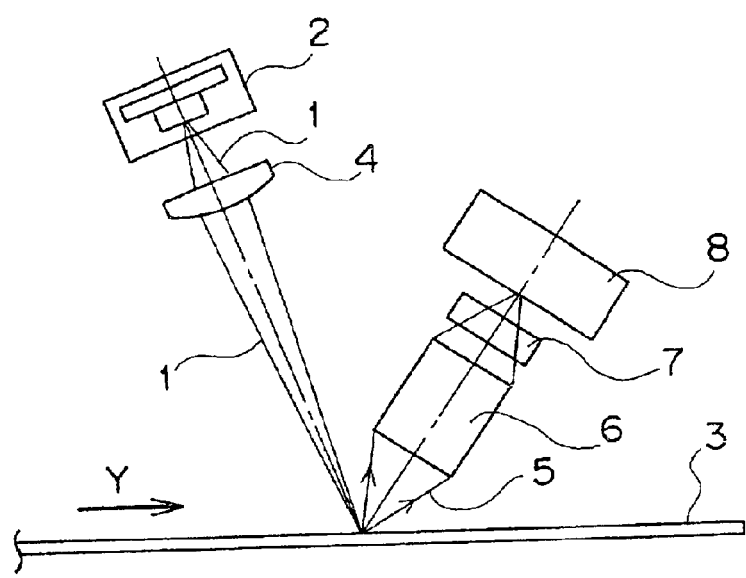
FIG. 2 is a schematic side view showing a reading optical system of a fluorescent image reading apparatus which is a preferred embodiment of the present invention.

FIG. 1 is a schematic perspective view showing a fluorescent image reading apparatus which is a preferred embodiment of the present invention and FIG. 2 is a schematic side view showing a reading optical system of the fluorescent image reading apparatus.

The fluorescent image reading apparatus according to this embodiment is constituted so as to photoelectrically detect residual fluorescence emission released from a fluorescent dye after the completion of irradiation with a stimulating ray, namely, a laser beam, and produce digital image data.

As shown in FIGS. 1 and 2, the fluorescent image reading apparatus according to this embodiment includes a laser diode array 2 for emitting a laser beam 1, a cylindrical lens 4 for condensing the laser beam 1 onto a gel support 3 which is an image carrier and carries an image of a fluorescent dye labeling a specimen, a lens array 6 for condensing fluorescence emission 5 released from the fluorescent dye contained in the gel support 3 upon being stimulated by the laser beam 1, a stimulating ray cut filter 7 disposed in the path of fluorescence emission 5 passing through the lens array 6 for cutting a light component having a wavelength equal to that of the laser beam 1 emitted from the laser diode array 2 and transmitting light components having wavelengths longer than that of the laser beam 1, a cooled CCD line sensor 8 for detecting only fluorescence emission passing through the stimulating ray cut filter 7, and an endless belt 9 for intermittently moving the gel support 3 in the direction indicated by an arrow Y in FIG. 1, namely, perpendicularly to the longitudinal direction X of the area to be irradiated with the laser beam 1 on the gel support 3.

As shown in FIG. 1, the fluorescent image reading apparatus according to this embodiment further includes an amplifier 10 for amplifying an analog signal produced by and output from the cooled CCD line sensor 8 with a predetermined amplifying factor, an A/D converter 11 for converting the analog signal amplified by the amplifier 10 into a digital image signal with a scale factor suitable for the signal fluctuation width, an image data buffer 12 for receiving and temporarily storing the digital image signal output from the A/D converter 11, and an image data storing means 13 for storing digital image data.

The digital image data temporarily stored in the image data buffer 12 are output to the image data storing means 13 at a predetermined time and stored therein. The digital image data stored in the image data storing means 13 are output to an image processing device 15 in accordance with an instruction signal from the user and are subjected to image processing as occasion demands and a fluorescent image is displayed on a display means such as a CRT or a flat display panel such as a liquid crystal display, an organic EL display or the like, based the digital image data.

Figure 3:
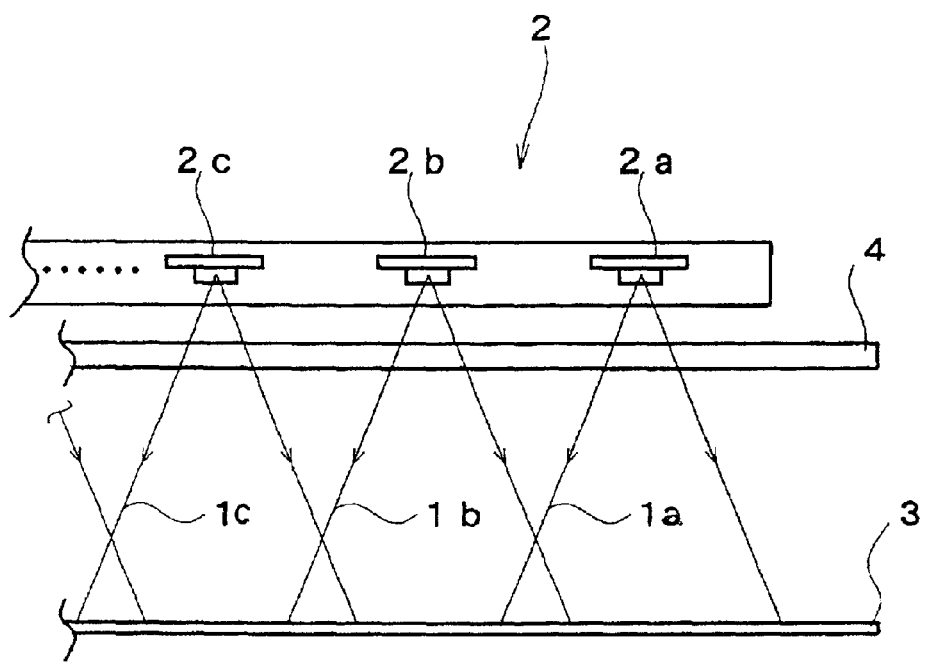
FIG. 3 is a schematic front view showing the details of a reading optical system of a fluorescent image reading apparatus which is a preferred embodiment of the present invention.

FIG. 3 is a schematic front view showing the details of a reading optical system of a fluorescent image reading apparatus which is a preferred embodiment of the present invention.

As shown in FIG. 3, the laser diode array 2 is constituted by arranging a plurality of laser diodes 2a, 2b, 2c, . . . in a single line and a laser beam 1a, 1b, 1c, divergently emitted from each of the laser diodes 2a, 2b, 2c, . . . is condensed in a single direction to form a fan-like laser beam 1 that linearly irradiates the gel support 3.

In this embodiment, since SYPRO Ruby (registered trademark) used as a fluorescent dye for labeling a specimen can be stimulated by a laser beam 1 having a wavelength of 473 nm, the plurality of laser diodes 2a, 2b, 2c, . . . are constituted so as to emit a laser beam having a wavelength of 473 nm. Therefore, a cut filter for cutting a light component having a wavelength of 473 nm and transmitting light components having longer wavelength than 473 nm is employed as a stimulating ray cut filter 7.

Figure 4:
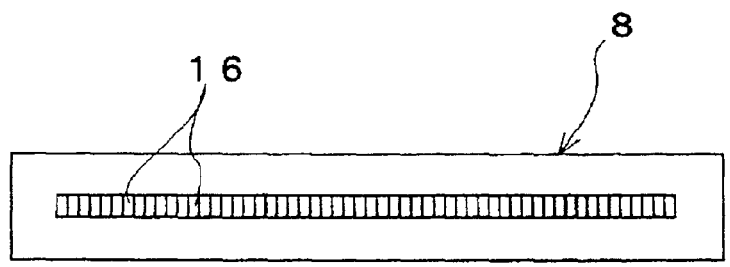
FIG. 4 is a schematic front view showing a cooled CCD line sensor used for a fluorescent image reading apparatus which is a preferred embodiment of the present invention.

FIG. 4 is a schematic front view showing the cooled CCD line sensor 8 used for a fluorescent image reading apparatus which is a preferred embodiment of the present invention.

As shown in FIG. 4, the cooled CCD line sensor 8 is constituted by arranging a plurality of sensor chips (photoelectrical conversion elements) 16 in a single line. The plurality of sensor chips 16 are disposed along the longitudinal direction of an area to be irradiated with the laser beam 1 on the gel support 3 as indicated by an arrow X in FIG. 1.

Although not shown in FIG. 4, the cooled CCD line sensor 8 is provided with a cooling means including a heat transfer plate made of a metal such as aluminum, a Peltier element for cooling the sensor chips (photoelectrical conversion elements) 16 and heat dispersion fins for dispersing heat generated by the Peltier element.

Figure 5:
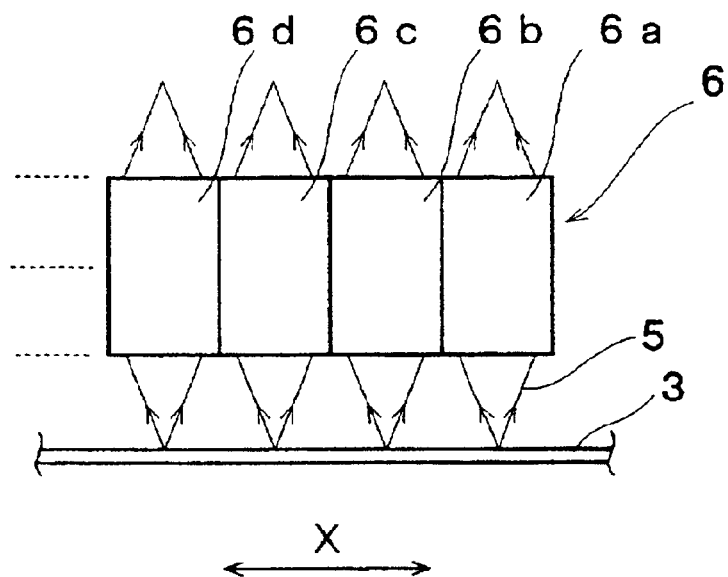
FIG. 5 is a schematic front view showing a lens array used for a fluorescent image reading apparatus which is a preferred embodiment of the present invention.
Figure 6:
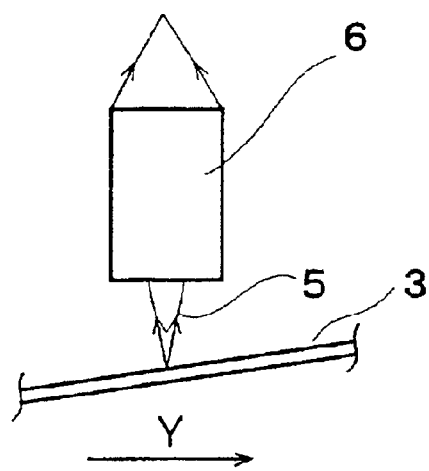
FIG. 6 is a schematic side view showing a lens array used for a fluorescent image reading apparatus which is a preferred embodiment of the present invention.

FIG. 5 is a schematic front view showing a lens array used for a fluorescent image reading apparatus which is a preferred embodiment of the present invention and FIG. 6 is a schematic side view thereof.

As shown in FIGS. 5 and 6, the lens array 6 is constituted by arranging many gradient index lenses 6a, 6b, 6c, 6d, . . . in a single line. The many gradient index lenses 6a, 6b, 6c, 6d, . . . are disposed along the longitudinal direction of an area to be irradiated with the laser beam 1 on the gel support 3 as indicated by the arrow X in FIG. 1.

Figure 7:
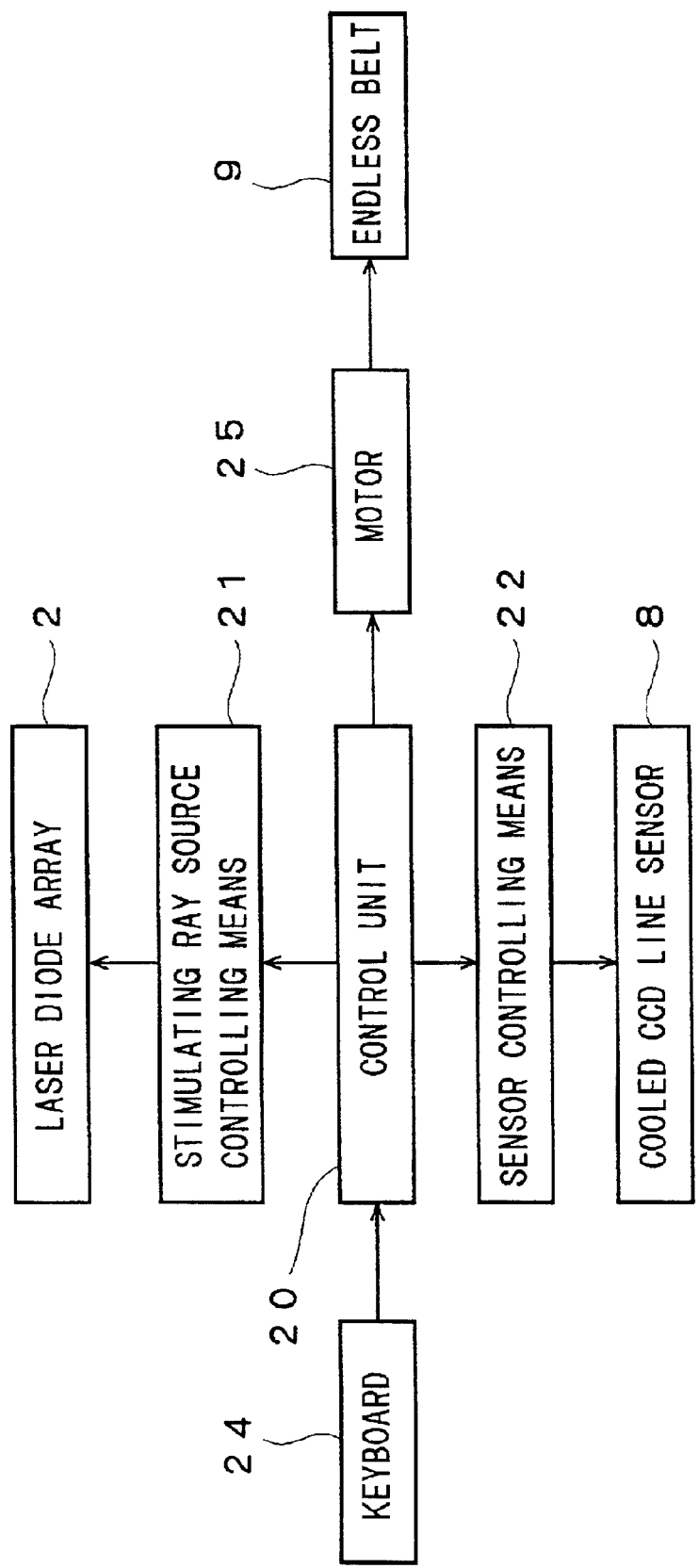
FIG. 7 is a block diagram of a control system, an input system and a drive system of a fluorescent image reading apparatus which is a preferred embodiment of the present invention.

FIG. 7 is a block diagram of a control system, an input system and a drive system of the fluorescent image reading apparatus which is a preferred embodiment of the present invention.

As shown in FIG. 7, the control system of the fluorescent image reading apparatus according to this embodiment includes a control unit 20 for controlling the overall operation of the fluorescent image reading apparatus, a stimulating ray source controlling means 21 for controlling the on-off operation of the plurality of laser diodes 2a, 2b, 2c, . . . constituting the laser diode array 2 and a sensor controlling means 22 for controlling the on-off operation of the plurality of sensor chips (photoelectrical conversion elements) 16 constituting the cooled CCD line sensor 8.

Further, as shown in FIG. 7, the input system of the fluorescent image reading apparatus according to this embodiment includes a keyboard 24 and the drive system thereof includes a motor 25 for driving the endless belt 9.

The thus constituted fluorescent image reading apparatus according to this embodiment irradiates the gel support 3 with a laser beam 1, photoelectrically detects residual fluorescence emission to read an image of a fluorescent dye labeling a specimen carried in the gel support 3 and produces digital image data in the following manner.

The gel support 3 carrying an image of a fluorescent dye labeling a specimen is first placed on the endless belt 9.

The kind of a fluorescent dye labeling the specimen is then input through the keyboard 24 together with a start signal.

In this embodiment, the gel support 3 carries an electrophoresis image of protein molecules labeled with a fluorescent dye.

The electrophoresis image of protein molecules labeled with a fluorescent dye is recorded in the gel support 3 by dying and labeling electrophoresed protein on the gel support 3 with, for example, SYPRO Ruby (registered trademark).

The start signal and the kind of a fluorescent dye labeling the specimen input through the keyboard 24 are input to the control unit 20 and when the control unit 20 receives the start signal, it outputs a drive signal to the motor 25 to cause it to drive the endless belt 9 until the gel support 3 placed on the endless belt 9 reaches a position where it can be irradiated with a laser beam 1.

A table in which light emitting amount data and decay times of residual fluorescence emission for each kind of fluorescent dye are written is produced in advance and stored in the control unit 20 and the control unit 20 accesses the table to read light emitting amount data and the decay time T of residual fluorescence emission of SYPRO Ruby (registered trademark) and stores them in a stimulation and detection control data memory (not shown).

The control unit 20 then determines, based on the light emitting amount data of residual fluorescence emission for SYPRO Ruby (registered trademark) read out from the table and stored in the stimulation and detection control data memory, how many times the step of irradiation with a laser beam 1 and detection of residual fluorescence emission should be repeated and stores the number n of repetition (n is an integer equal to or greater than 1) in the stimulation and detection control data memory. Since the amount of residual fluorescence emission is generally small, this embodiment is constituted so that the step of irradiation with a laser beam 1 and detection of residual fluorescence emission can be repeated in order to receive a sufficient light amount of residual fluorescence emission.

At the same time, based on the decay time T of residual fluorescence emission of the fluorescent dye labeling the specimen read from the table, the control unit 20 determines the time period T1 during which the plurality of laser diodes 2a, 2b, 2c, . . . constituting the laser diode array 2 are held on and the fluorescent dye is stimulated by the laser beam 1, the time tssi when the plurality of laser diodes 2a, 2b, 2c, . . . are turned on and the time tsei when the plurality of laser diodes 2a, 2b, 2c, . . . are turned off and further determines the time period T2 during which the plurality of sensor chips (photoelectrical conversion elements) 16 constituting the cooled CCD line sensor 8 are held on and fluorescence emission released from the fluorescent dye is detected by the plurality of sensor chips 16, the time tdsi when the plurality of sensor chips 16 are turned on and the time tdei when the plurality of sensor chips 16 are turned off. The control unit 20 then stores the determined values in the stimulation and detection control data memory and outputs a stimulating ray irradiation start signal to the stimulating ray source control means 21.

Here, i designates the ith step of irradiation with a laser beam 1 and detection of residual fluorescence emission.

Figure 8:
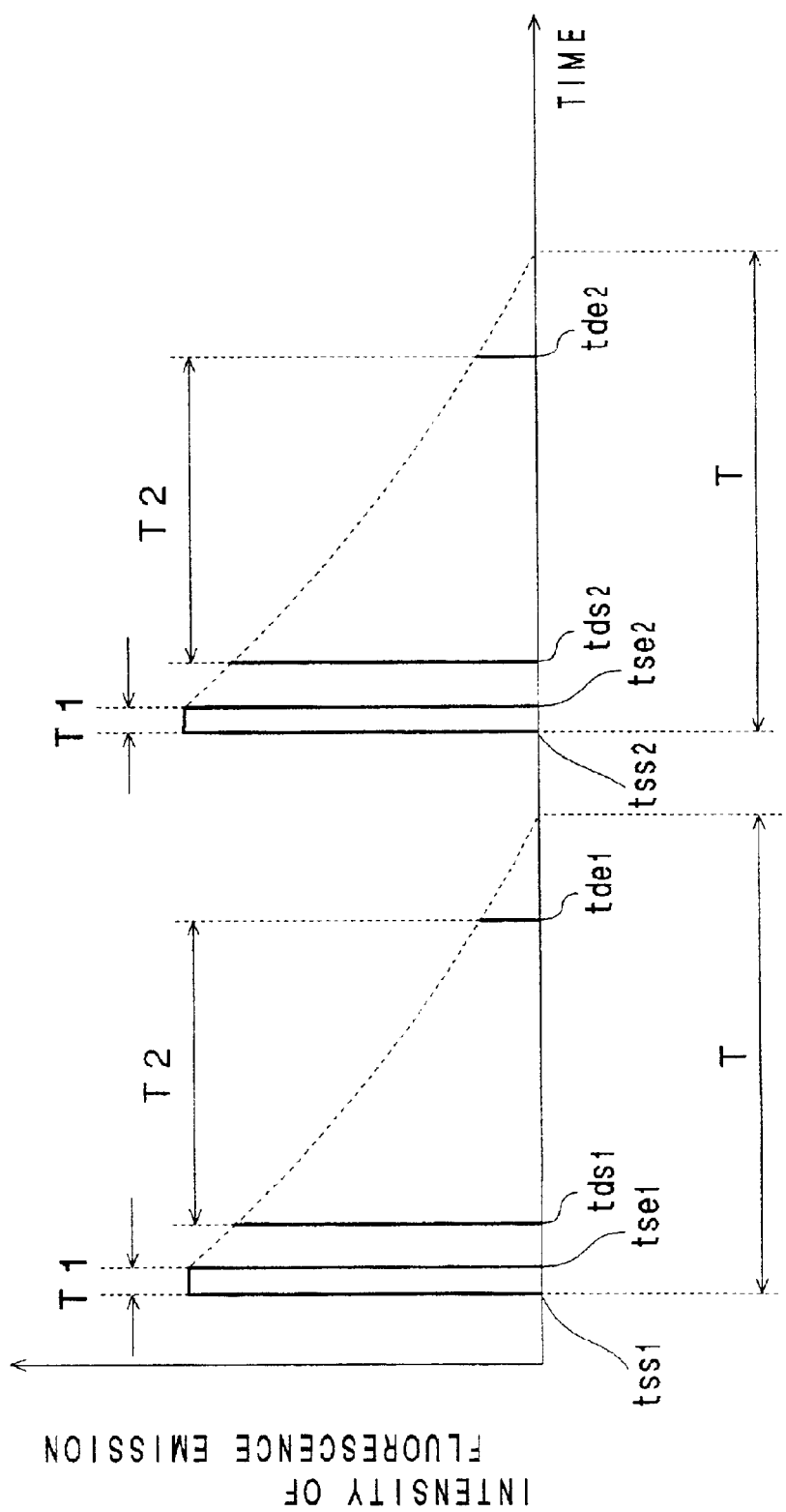
FIG. 8 is a graph showing the relationship between irradiation time with a laser beam and the intensity of fluorescence emission released from a fluorescent dye.

FIG. 8 is a graph showing the relationship between irradiation time with the laser beam 1 and the intensity of fluorescence emission released from the fluorescent dye.

As shown in FIG. 8, the output of the stimulating ray irradiation start signal from the control unit 20 to the stimulating ray source control means 21, turns on the plurality of laser diodes 2a, 2b, 2c, . . . constituting the laser diode array 2 at the time tss1 so that laser beams 1 having a wavelength of 473 nm are divergently emitted.

Each of the laser beams 1 divergently emitted is condensed by the cylindrical lens 4 in a single direction to form a fan-like laser beam 1 and the gel support 3 is linearly irradiated with the fan-like laser beam 1.

As a result, SYPRO Ruby (registered trademark) which is a fluorescent dye contained in the gel support 3 and labeling the specimen is stimulated to release fluorescence emission. However, since the plurality of sensor chips 16 constituting the cooled CCD line sensor 8 are held off while the plurality of laser diodes 2a, 2b, 2c, . . . constituting the laser diode array 2 are held on, fluorescence emission is not detected by the cooled CCD line sensor 8.

As shown in FIG. 8, at the time tse1 when the time period T1 has passed after the plurality of laser diodes 2a, 2b, 2c, . . . were turned on, the control unit 20 outputs a stimulating ray irradiation stop signal to the stimulating ray source controlling means 21, thereby causing it to turn off the plurality of laser diodes 2a, 2b, 2c, . . . constituting the laser diode array 2.

Even after the laser diodes 2a, 2b, 2c, . . . have been turned off and the laser beam 1 is no longer emitted, fluorescence emission called residual fluorescence emission continues to be released from SYPRO Ruby (registered trademark) which is a fluorescent dye contained in the gel support 3 and labeling the specimen.

As shown in FIG. 8, the control unit 20 outputs a light detection start signal to the sensor controlling means 22 at the time tds2, thereby causing it to turn on the plurality of sensor chips 16 constituting the cooled CCD line sensor 8.

As a result, residual fluorescence emission released from SYPRO Ruby (registered trademark) which is a fluorescent dye contained in the gel support 3 and labeling the specimen is condensed by the lens array 6 and enters the stimulating ray cut filter 7.

Since the stimulating ray cut filter 7 has a property of cutting a light component having a wavelength of 473 nm emitted from the laser diode array 2 and transmitting only light components having wavelengths longer than 473 nm, a light component having a wavelength of 473 nm equal to that of the laser beam 1 is cut by the stimulating ray cut filter 7 and only residual fluorescence emission having wavelengths longer than 473 nm equal to that of the laser beam 1 is transmitted through the stimulating ray cut filter 7 and enters the light receiving surfaces of the plurality of sensor chips 16 constituting the cooled CCD line sensor 8 to form an image on the light receiving surfaces.

The plurality of sensor chips 16 constituting the cooled CCD line sensor 8 receive light of the image thus formed on the light receiving surfaces and accumulate it in the form of electric charges therein.

As shown in FIG. 8, at the time tde1 when the time period T2 has passed after the plurality of sensor chips 16 constituting the cooled CCD line sensor 8 were turned on, the control unit 20 outputs a light detection stop signal to the sensor controlling means 22, thereby causing it to turn off the plurality of sensor chips 16 constituting the cooled CCD line sensor 8.

Thus, the first step of irradiation with a laser beam 1 and detection of residual fluorescence emission is completed.

Further, at the time tss2, as shown in FIG. 8, a second step of irradiation with a laser beam 1 and detection of residual fluorescence emission is started and the control unit 20 outputs a stimulating ray irradiation start signal to the stimulating ray source controlling means 21, thereby again causing it to turn on the plurality of laser diodes 2a, 2b, 2c, . . . constituting the laser diode array 2.

As a result, laser beams 1 having a wavelength of 473 nm are divergently emitted from the plurality of laser diodes 2a, 2b, 2c, . . . and each of the laser beams 1 is condensed by the cylindrical lens 4 in a single direction to form a fan-like laser beam 1 that linearly irradiates the gel support 3.

When the gel support 3 is irradiated with the laser beam 1, SYPRO Ruby (registered trademark) which is a fluorescent dye contained in the gel support 3 and labeling the specimen is stimulated to release fluorescence emission. However, since the plurality of sensor chips 16 constituting the cooled CCD line sensor 8 are held off while the plurality of laser diodes 2a, 2b, 2c, . . . constituting the laser diode array 2 are held on, fluorescence emission is not detected by the cooled CCD line sensor 8.

As shown in FIG. 8, at the time tse2 when the time period T1 has passed after the plurality of laser diodes 2a, 2b, 2c, . . . were turned on, the control unit 20 outputs a stimulating ray irradiation stop signal to the stimulating ray source controlling means 21, thereby causing it to turn off the plurality of laser diodes 2a, 2b, 2c, . . . constituting the laser diode array 2.

Further, as shown in FIG. 8, the control unit 20 outputs a light detection start signal to the sensor controlling means 22 at the time tds2, thereby causing it to turn on the plurality of sensor chips 16 constituting the cooled CCD line sensor 8.

As a result, residual fluorescence emission released from SYPRO Ruby (registered trademark) which is a fluorescent dye contained in the gel support 3 and labeling the specimen after the completion of irradiation with the laser beam 1 is condensed by the lens array 6 and enters the stimulating ray cut filter 7.

A light component having a wavelength of 473 nm equal to that of the laser beam 1 is cut by the stimulating ray cut filter 7 and only residual fluorescence emission having wavelengths longer than 473 nm equal to that of the laser beam 1 is transmitted through the stimulating ray cut filter 7 and enters the light receiving surfaces of the plurality of sensor chips 16 constituting the cooled CCD line sensor 8 to form an image on the light receiving surfaces.

The plurality of sensor chips 16 constituting the cooled CCD line sensor 8 receive light of the image thus formed on the light receiving surfaces and accumulate it in the form of electric charges therein.

As shown in FIG. 8, at the time tde2 when the time period T2 has passed after the plurality of sensor chips 16 constituting the cooled CCD line sensor 8 were turned on, the control unit 20 outputs a light detection stop signal to the sensor controlling means 22, thereby causing it to turn off the plurality of sensor chips 16 constituting the cooled CCD line sensor 8.

Thus, the second step of irradiation with a laser beam 1 and detection of residual fluorescence emission is completed.

Similarly to the above, the step of irradiation with a laser beam 1 and detection of residual fluorescence emission is repeated and when the number of the repeated steps becomes equal to the number n of repetition stored in the stimulation and detection control data memory, the control unit 20 causes the plurality of sensor chips 16 constituting the cooled CCD line sensor 8 to output analog image data accumulated in the form of electric charge therein to the amplifier 10 and causes the amplifier 10 to amplify the analog image data with a predetermined amplifying factor. The control unit 20 further causes the amplifier 10 to output amplified analog image data to the A/D converter 11, causes the A/D converter 11 to convert the analog image data to digital image data with a scale factor suitable for the signal fluctuation width and temporarily stores the digital image data in the image data buffer 12.

At the same time, the control unit 20 outputs a drive signal to the motor 25, thereby causing it to move the endless belt 9 by a distance equal to one scanning line in the direction indicated by the arrow Y in FIG. 1.

Similarly, an adjacent linear area of the gel support 3 is irradiated with laser beams 1 having a wavelength of 473 nm and emitted from the plurality of laser diodes 2a, 2b, 2c, . . . constituting the laser diode array 2 and SYPRO Ruby (registered trademark) which is a fluorescent dye contained in the gel support 3 and labeling the specimen is stimulated. Residual fluorescence emission released from SYPRO Ruby (registered trademark) which is a fluorescent dye contained in the gel support 3 and labeling the specimen after the completion of irradiation with the laser beam 1 is received by the plurality of sensor chips 16 constituting the cooled CCD line sensor 8 and accumulated in the form of electric charge therein.

Thus, when an nth step of irradiation with a laser beam 1 and detection of residual fluorescence emission has been completed, the control unit 20 causes the plurality of sensor chips 16 constituting the cooled CCD line sensor 8 to output analog image data accumulated in the form of electric charge therein to the amplifier 10 and causes the amplifier 10 to amplify the analog image data with a predetermined amplifying factor. The control unit 20 further causes the amplifier 10 to output amplified analog image data to the A/ID converter 11, causes the A/D converter 11 to convert the analog image data to digital image data with a scale factor suitable for the signal fluctuation width and temporarily stores the digital image data in the image data buffer 12.

At the same time, the control unit 20 outputs a drive signal to the motor 25, thereby causing it to move the endless belt 9 by a distance equal to one scanning line in the direction indicated by the arrow Y in FIG. 1.

Thus, the whole surface of the gel support 3 is scanned with laser beams 1 having a wavelength of 473 nm and emitted from the plurality of laser diodes 2a, 2b, 2c, . . . constituting the laser diode array 2 and residual fluorescence emission released from SYPRO Ruby (registered trademark) which is a fluorescent dye is detected by the plurality of sensor chips 16 constituting the cooled CCD line sensor 8 to produce analog image data. The analog image data are digitized by the A/D converter 11 and an image of the fluorescent dye labeling the specimen carried in the gel support 3 is read. The thus produced digital image data are temporarily stored in the image data buffer 12.

When an image of the fluorescent dye labeling the specimen carried in one gel support 3 has been read, a data transfer signal is output from the control unit 20 to the image data buffer 12 and the digital image data temporarily stored in the image data buffer 12 are output to the image data storing means 13 and stored therein.

When the user requests production of a fluorescent image by inputting an image producing signal through the keyboard 24, the control unit 20 outputs the digital image data stored in the image data storing means 13 to the image processing device 15.

The image processing device 15 effects necessary image processing on the thus input digital image data in accordance with the user's instructions and a fluorescent image is displayed on a display means such as a CRT or a flat display panel such as a liquid crystal display, an organic EL display or the like based on the image processed digital image data.

According to the above described embodiment, although a linear area of the gel support 3 is irradiated with the linear laser beams 1 having a wavelength of 473 nm, emitted from the plurality of laser diodes 2a, 2b, 2c, . . . constituting the laser diode array 2 and condensed by the cylindrical lens 4 in a single direction and SYPRO Ruby (registered trademark) which is a fluorescent dye contained in the gel support 3 and labeling the specimen is stimulated, since the plurality of sensor chips 16 constituting the cooled CCD line sensor 8 are held off while the gel support 3 is irradiated with the linear laser beams 1, fluorescence emission is not detected by the cooled CCD line sensor 8. After the plurality of laser diodes 2a, 2b, 2c, . . . constituting the laser diode array 2 have been turned off, the plurality of sensor chips 16 constituting the cooled CCD line sensor 8 are turned on and residual fluorescence emission released from SYPRO Ruby (registered trademark) which is a fluorescent dye contained in the gel support 3 and labeling the specimen after the completion of irradiation with the laser beams 1 is detected by the plurality of sensor chips 16 constituting the cooled CCD line sensor 8. The analog image data produced by the cooled CCD line sensor 8 are digitized by the A/D converter 11 to produce digital image data. Therefore, since the plurality of laser diodes 2a, 2b, 2c, . . . constituting the laser diode array 2 have been already turned off when the plurality of sensor chips 16 constituting the cooled CCD line sensor 8 detect residual fluorescence emission, it is possible to prevent noise caused by detecting the laser beams 1 by the plurality of sensor chips 16 constituting the cooled CCD line sensor 8 from being generated in the digital image data and to improve an S/N ratio.

Further, according to the above described embodiment, since all the fluorescent dye contained in a linear area of the gel support 3 is simultaneously stimulated by irradiating the linear area of the gel support with the linear laser beams 1 having a wavelength of 473 nm, emitted from the plurality of laser diodes 2a, 2b, 2c, . . . constituting the laser diode array 2 and condensed by the cylindrical lens 4 in a single direction, even if the step of irradiation with the linear laser beams 1 and detection of residual fluorescence emission is repeated in order to increase the amount of residual fluorescence emission to be received by the cooled CCD line sensor 8, it is still possible to rapidly produce digital image data in which noise caused by photoelectrically detecting the laser beams 1 by the plurality of sensor chips 16 constituting the cooled CCD line sensor 8 is lowered and which have a high S/N ratio.

Furthermore, according to the above described embodiment, since the fluorescent image reading apparatus is provided with the stimulating ray cut filter 7 having a property of cutting a light component having a wavelength of the laser beam 1 emitted from the laser diode array 2 and transmitting only light components having wavelengths longer than that of the laser beam 1, it is possible to produce digital image data in which noise caused by photoelectrically detecting the laser beams 1 by the plurality of sensor chips 16 constituting the cooled CCD line sensor 8 is markedly lowered and which have a high S/N ratio.

Figure 9:
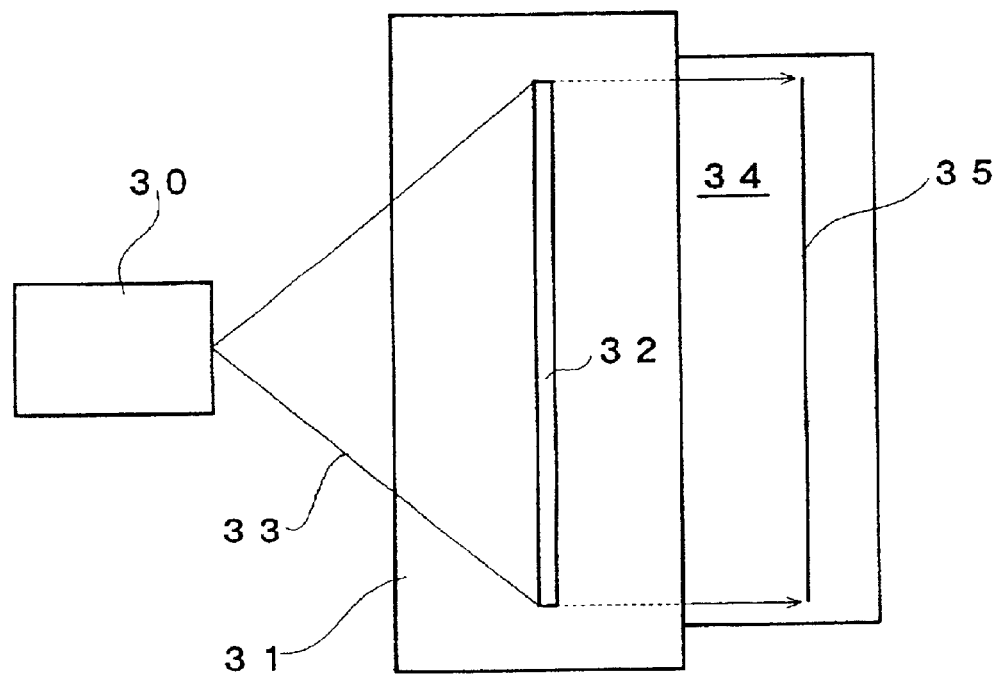
FIG. 9 is a schematic plan view showing a fluorescent image reading apparatus which is another preferred embodiment of the present invention in the vicinity of a stimulating ray source.

FIG. 9 is a schematic plan view showing the vicinity of a stimulating ray source of a fluorescent image reading apparatus which is another preferred embodiment of the present invention.

As shown in FIG. 9, a fluorescent image reading apparatus according to this embodiment is provided with an LED stimulating ray source 30 and a light blocking plate 31 and the light blocking plate 31 is formed with a linear slit 32.

In this embodiment, an LED stimulating ray source 30 for emitting a stimulating ray 33 having a center wavelength of 340 nm is employed instead of the laser diode array 2 in the previous embodiment and the light blocking plate 31 is formed of a material capable of cutting at least a light component having a wavelength of 340 nm. The width of the slit 32 is determined so as to coincide with the width of an image carrying area of an image carrier 34 carrying an image of a fluorescent dye labeling a specimen.

Therefore, a part of a stimulating ray 33 having a wavelength of 340 nm and emitted from the LED stimulating ray source 30 is cut by the light blocking plate 31 and only a line beam of the stimulating ray 33 passing through the slit 32 is projected onto the image carrier 34, thereby simultaneously stimulating all the fluorescent dye contained in a linear area 35 of the image carrier 34.

Figure 10:
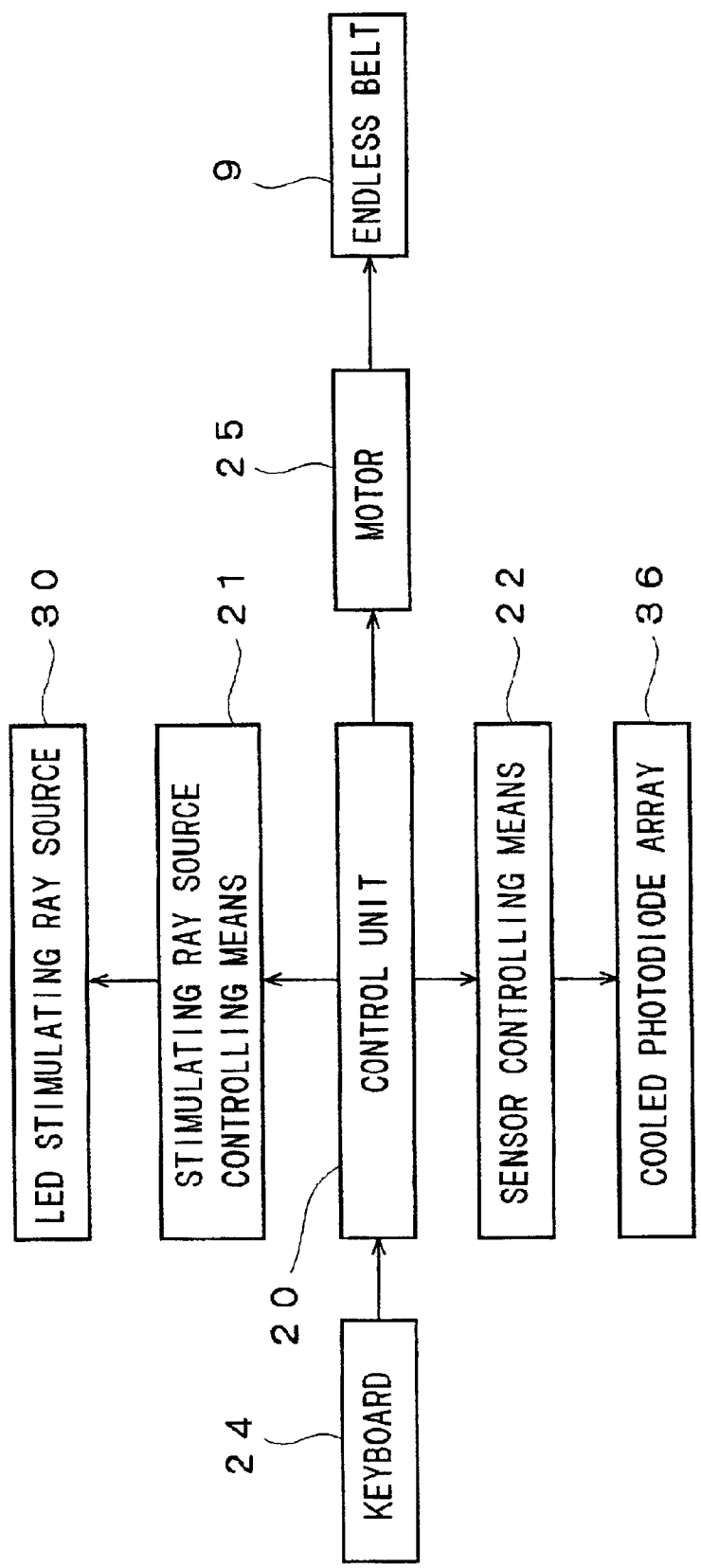
FIG. 10 is a block diagram of a control system, an input system and a drive system of a fluorescent image reading apparatus which is another preferred embodiment of the present invention.

FIG. 10 is a block diagram of a control system, an input system and a drive system of the fluorescent image reading apparatus according to this embodiment.

As shown in FIG. 10, in this embodiment, a cooled photodiode array 36 provided with a cooling means (not shown) is employed instead of the cooled CCD line sensor 8 in the previous embodiment and, therefore, the control system, the input system and the drive system of the fluorescent image reading apparatus according to this embodiment has the same configuration as that of the fluorescent image reading apparatus according the embodiment shown in FIG. 7 except that the stimulating ray source control means 21 is constituted so as to control the on-off operation of the LED stimulating ray source 30 and that the sensor controlling means 22 is constituted so as to control the on-off operation of the cooled photodiode array 36.

In this embodiment, a membrane filter is used as the image carrier 34 and the membrane filter 34 carries an electrophoresis image of protein molecules labeled with a fluorescent dye.

The electrophoresis image of protein molecules labeled with a fluorescent dye is recorded in the membrane filter 34 by dying and labeling electrophoresed protein on the membrane filter 34 with, for example, DELFIA (registered trademark).

The thus constituted fluorescent image reading apparatus according to this embodiment irradiates the membrane filter 34 with a line beam of a stimulating ray 33, photoelectrically detects residual fluorescence emission to read an image of a fluorescent dye labeling a specimen carried in the membrane filter 34 and produce digital image data in the following manner.

The membrane filter 34 carrying an image of a fluorescent dye labeling a specimen is first placed on the endless belt 9.

DELFIA (registered trademark) is then input as the kind of fluorescent dye labeling the specimen through the keyboard 24 together with a start signal.

The start signal and the kind of a fluorescent dye labeling the specimen input through the keyboard 24 are input to the control unit 20 and when the control unit 20 receives the start signal, it outputs a drive signal to the motor 25 to cause it to drive the endless belt 9 until the membrane filter 34 placed on the endless belt 9 reaches a position where it can be irradiated with the line beam of the stimulating ray 33.

At the same time, the control unit 20 accesses the table in which light emitting amount data and decay times of residual fluorescence emission for each kind of fluorescent dye are written, reads light emitting amount data and the decay time T of residual fluorescence emission of DELFIA (registered trademark) and stores them in a stimulation and detection control data memory (not shown).

The control unit 20 then determines, based on light emitting amount data of residual fluorescence emission for DELFIA (registered trademark) read out from the table and stored in the stimulation and detection control data memory, how many times the step of irradiation with the line beam of the stimulating ray 33 and detection of residual fluorescence emission should be repeated and stores the number m of repetition (m is an integer equal to or greater than 1) in the stimulation and detection control data memory.

At the same time, based on the decay time T of residual fluorescence emission of DELFIA which is a fluorescent dye labeling the specimen read from the table, the control unit 20 determines the time period T1 during which the LED stimulating ray source 30 is held on and the fluorescent dye is stimulated by the stimulating ray 33, the time tssi when the LED stimulating ray source 30 is turned on and the time tsei when the LED stimulating ray source 30 is turned off and further determines the time period T2 during which the cooled photodiode array 36 is held on and fluorescence emission released from the fluorescent dye is detected by the cooled photodiode array 36, the time tdsi when the cooled photodiode array 36 is turned on and the time tdei when the cooled photodiode array 36 is turned off. The control unit 20 then stores the determined values in the stimulation and detection control data memory and outputs a stimulating ray irradiation start signal to the stimulating ray source control means 21.

As a result, the LED stimulating ray source 30 is turned on at the time tss1 and a stimulating ray 33 having a center wavelength of 340 nm is divergently emitted.

A part of the stimulating ray 33 divergently emitted from the LED stimulating ray source 30 is cut by the light blocking plate 31 and only the line beam of the stimulating ray 33 passing through the slit 32 is projected onto the membrane filter 34.

As a result, DELFIA (registered trademark) which is a fluorescent dye contained in a linear area 35 of the membrane filter 34 is simultaneously stimulated throughout the linear 35 to release fluorescence emission. However, since the cooled photodiode array 36 is held off while the LED stimulating ray source 30 is held on, fluorescence emission is not detected by the cooled photodiode array 36.

At the time tse1 when the time period T1 has passed after the LED stimulating ray source 30 was turned on, the control unit 20 outputs a stimulating ray irradiation stop signal to the stimulating ray source controlling means 21, thereby causing it to turn off the LED stimulating ray source 30.

Even after the LED stimulating ray source 30 has been turned off and the line beam of the stimulating ray 33 is no longer emitted, fluorescence emission called residual fluorescence emission continues to be released from DELFIA (registered trademark) which is a fluorescent dye contained in the membrane filter 34 and labeling the specimen.

The control unit 20 outputs a light detection start signal to the sensor controlling means 22 at the time tds1, thereby causing it to turn on the cooled photodiode array 36.

As a result, residual fluorescence emission released from DELFIA (registered trademark) which is a fluorescent dye contained in the membrane filter 34 and labeling the specimen is condensed by the lens array 6 and enters the stimulating ray cut filter 7.

In this embodiment, a cut filter having a property of cutting a light component having a wavelength of 340 nm equal to that of the stimulating ray 33 and transmitting only light components having wavelengths longer than 340 nm is employed as a stimulating ray cut filter 7. Therefore, a light component having a wavelength of 340 nm equal to that of the stimulating ray 33 is cut by the stimulating ray cut filter 7 and only residual fluorescence emission having wavelengths longer than 340 nm equal to that of the stimulating ray 33 is transmitted through the stimulating ray cut filter 7 and enters the light receiving surface of the cooled photodiode array 36 to form an image on the light receiving surface.

The cooled photodiode array 36 receives light of the image thus formed on the light receiving surface and accumulates it in the form of electric charges therein.

At the time tde1 when the time period T2 has passed after the cooled photodiode array 36 was turned on, the control unit 20 outputs a light detection stop signal to the sensor controlling means 22, thereby causing it to turn off the cooled photodiode array 36.

Thus, the first step of irradiation with the stimulating ray 33 and detection of residual fluorescence emission is completed.

Further, a second step of irradiation with the stimulating ray 33 and detection of residual fluorescence emission is started at the time tss2 and the control unit 20 outputs a stimulating ray irradiation start signal to the stimulating ray source controlling means 21, thereby again causing it to turn on the LED stimulating ray source 30.

As a result, the stimulating ray 33 having a center wavelength of 340 nm is divergently emitted from the LED stimulating ray source 30.

A part of the stimulating ray 33 divergently emitted from the LED stimulating ray source 30 is cut by the light blocking plate 31 and only the line beam of the stimulating ray 33 passing through the slit 32 is projected onto the membrane filter 34.

As a result, DELFIA (registered trademark) which is a fluorescent dye contained in a linear area 35 of the membrane filter 34 is simultaneously stimulated throughout the linear area 35 to release fluorescence emission. However, since the cooled photodiode array 36 is held off while the LED stimulating ray source 30 is held on, fluorescence emission is not detected by the cooled photodiode array 36.

At the time tse2 when the time period T1 has passed after the LED stimulating ray source 30 was turned on, the control unit 20 outputs a stimulating ray irradiation stop signal to the stimulating ray source controlling means 21, thereby causing it to turn off the LED stimulating ray source 30.

The control unit 20 then outputs a light detection start signal to the sensor controlling means 22 at the time tds2, thereby causing it to turn on the cooled photodiode array 36.

As a result, residual fluorescence emission released from DELFIA (registered trademark) which is a fluorescent dye contained in the membrane filter 34 and labeling the specimen is condensed by the lens array 6 and enters the stimulating ray cut filter 7.

Since the stimulating ray cut filter 7 has a property of cutting a light component having a wavelength of 340 nm equal to that of the stimulating ray 33 and transmitting only light components having wavelengths longer than 340 nm, a light component having a wavelength of 340 nm equal to that of the stimulating ray 33 is cut by the stimulating ray cut filter 7 and only residual fluorescence emission having wavelengths longer than 340 nm equal to that of the stimulating ray 33 is transmitted through the stimulating ray cut filter 7 and enters the light receiving surfaces of the cooled photodiode array 36 to form an image on the light receiving surfaces.

The cooled photodiode array 36 receives light of the image thus formed on the light receiving surfaces and accumulates it in the form of electric charges therein.

Thus, the second step of irradiation with the stimulating ray 33 and detection of residual fluorescence emission is completed.

Similarly to the above, the step of irradiation with the stimulating ray 33 and detection of residual fluorescence emission is repeated and when the number of the repeated steps becomes equal to the number m of repetition stored in the stimulation and detection control data memory, the control unit 20 causes an electric charge transfer means (not shown) to output analog image data accumulated in the form of electric charge by the cooled photodiode array 36 to the amplifier 10 and causes the amplifier 10 to amplify the analog image data with a predetermined amplifying factor. The control unit 20 further causes the amplifier 10 to output amplified analog image data to the A/D converter 11, causes the A/D converter 11 to convert the analog image data to digital image data with a scale factor suitable for the signal fluctuation width and temporarily stores the digital image data in the image data buffer 12.

At the same time, the control unit 20 outputs a drive signal to the motor 25, thereby causing it to move the endless belt 9 by a distance equal to one scanning line in the direction indicated by the arrow Y in FIG. 1.

Similarly, an adjacent linear area of the membrane filter 34 is irradiated with the stimulating ray 33 having a center wavelength of 340 nm and emitted from the LED stimulating ray source 30 and DELFIA (registered trademark) which is a fluorescent dye contained in the membrane filter 34 and labeling the specimen is stimulated. Residual fluorescence emission released from DELFIA (registered trademark) which is a fluorescent dye contained in the gel support 3 and labeling the specimen after the completion of irradiation with the stimulating ray 33 is received by the cooled photodiode array 36 and accumulated in the form of electric charge therein.

Thus, when an mth step of irradiation with the stimulating ray 33 and detection of residual fluorescence emission has been completed, the control unit 20 causes the electric charge transfer means (not shown) to output analog image data accumulated in the form of electric charge by the cooled photodiode array 36 to the amplifier 10 and causes the amplifier 10 to amplify the analog image data with a predetermined amplifying factor. The control unit 20 further causes the amplifier 10 to output amplified analog image data to the A/D converter 11, causes the A/D converter 11 to convert the analog image data to digital image data with a scale factor suitable for the signal fluctuation width and temporarily stores the digital image data in the image data buffer 12.

At the same time, the control unit 20 outputs a drive signal to the motor 25, thereby causing it to move the endless belt 9 by a distance equal to one scanning line in a direction indicated by an arrow Y in FIG. 1.

Thus, the whole surface of the membrane filter 34 is scanned with the stimulating ray 33 having a center wavelength of 340 nm and emitted from the LED stimulating ray source 30 and residual fluorescence emission released from DELFIA (registered trademark) which is a fluorescent dye is detected by the cooled photodiode array 36 to produce analog image data. The analog image data are digitized by the A/D converter 11 and an image of the fluorescent dye labeling the specimen carried in the gel support 3 is read. The thus produced digital image data are temporarily stored in the image data buffer 12.

When an image of the fluorescent dye labeling the specimen carried in one membrane filter 34 has been read, a data transfer signal is output from the control unit 20 to the image data buffer 12 and the digital image data temporarily stored in the image data buffer 12 are output to the image data storing means 13 and stored therein.

When the user requests production of a fluorescent image by imputting an image producing signal through the keyboard 24, the control unit 20 outputs the digital image data stored in the image data storing means 13 to the image processing device 15

The image processing device 15 effects necessary image processing on the thus input digital image data in accordance with the user's instructions and a fluorescent image is displayed on the display means such as a CRT or a flat display panel such as a liquid crystal display, an organic EL display or the like based on the image processed digital image data According to this embodiment, although a linear area of the membrane filter 34 is irradiated with the line beam of the stimulating ray 33 having a center wavelength of 340 nm and emitted from the LED stimulating ray source 30 and DELFIA (registered trademark) which is a fluorescent dye contained in the membrane filter 34 and labeling the specimen is stimulated, since the cooled photodiode array 36 is held off while the LED stimulating ray source 30 is held on, fluorescence emission is not detected by the cooled photodiode array 36. After the LED stimulating ray source 30 has been turned off, the cooled photodiode array 36 is turned on and residual fluorescence emission released from DELFIA (registered trademark) which is a fluorescent dye contained in the membrane filter 34 and labeling the specimen after the completion of irradiation with the stimulating ray 33 is detected by the cooled photodiode array 36. The analog image data produced by the cooled photodiode array 36 are digitized by the A/D converter 11 to produce digital image data. Therefore, since the LED stimulating ray source 30 has been already turned off when the cooled photodiode array 36 detects residual fluorescence emission, it is possible to prevent noise caused by detecting the stimulating ray 33 by the cooled photodiode array 36 from being generated in the digital image data and to improve an S/N ratio.

Further, according to this embodiment, since all the fluorescent dye contained in a linear area of the gel support 3 is simultaneously by irradiating the linear area of the membrane filter 34 with the line beam of the stimulating ray 33 having a center wavelength of 340 nm and emitted from the LED stimulating ray source 30, even if the step of irradiation with the stimulating ray 33 and detection of residual fluorescence emission is repeated in order to increase the amount of residual fluorescence emission to be received by the cooled photodiode array 36, it is still possible to rapidly produce digital image data in which noise caused by photoelectrically detecting the stimulating ray 33 by the cooled photodiode array 36 is lowered and which have a high S/N ratio.

Furthermore, according to this embodiment, since the fluorescent image reading apparatus is provided with the stimulating ray cut filter 7 having a property of cutting a light component having a wavelength of the stimulating ray 33 emitted from the LED stimulating ray source 30 and transmitting only light components having wavelengths longer than that of the stimulating ray 33, it is possible to produce digital image data in which noise caused by photoelectrically detecting the stimulating ray 33 by the cooled photodiode array 36 is markedly lowered and which have a high S/N ratio.

Figure 11:
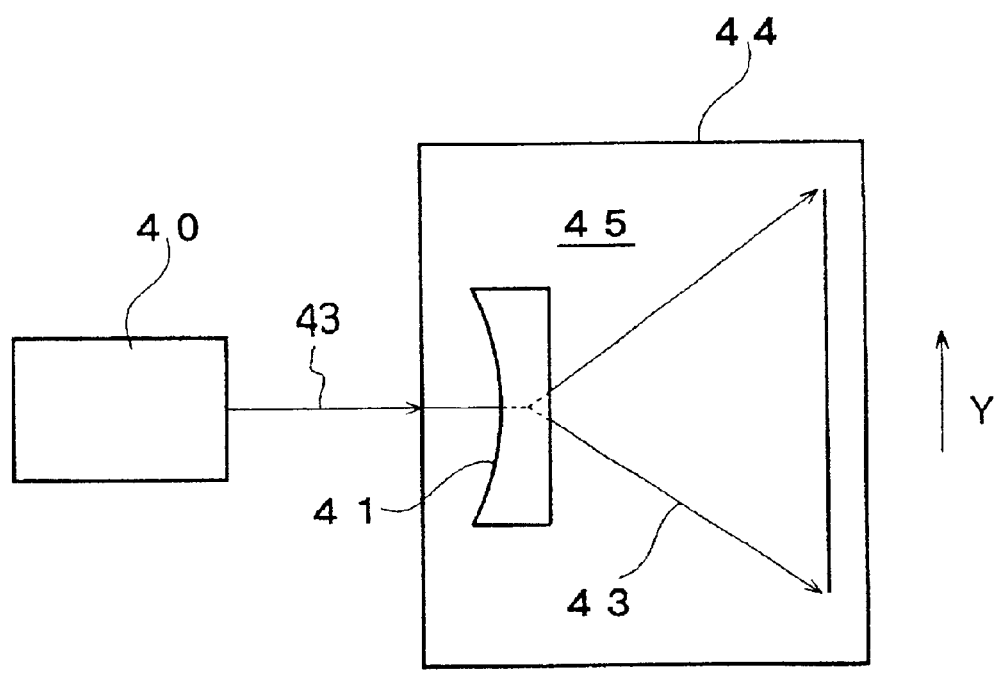
FIG. 11 is a schematic plan view showing the vicinity of a stimulating ray source of an autoradiographic image reading apparatus which is a further preferred embodiment of the present invention.

FIG. 11 is a schematic plan view showing the vicinity of a stimulating ray source of an autoradiographic image reading apparatus which is a further preferred embodiment of the present invention.

As shown in FIG. 11, an autoradiographic image reading apparatus according to this embodiment is provided with a laser stimulating ray source 40 and a lens 41.

In this embodiment, a laser stimulating ray source 40 for emitting a laser beam 43 having a wavelength of 640 nm is employed instead of the laser diode array 2 according to the embodiment shown in FIGS. 1 to 8 and as shown in FIG. 11, the laser beam 43 emitted from the laser stimulating ray source 40 is diverged by the lens 41 in the direction indicated by the arrow Y in FIG. 11 and corresponding to the direction indicated by the arrow Y in FIG. 1 and is converged in a plane including the optical axis and the longitudinal axis of the lens 41 by the lens 41 in a direction perpendicular to the direction indicated by the arrow Y.

As a result, a linear laser beam 43 is generated and is linearly projected onto a stimulable phosphor layer 45 of a stimulable phosphor sheet 44 carrying an autoradiographic image, thereby simultaneously exciting all the stimulable phosphor contained in a linear area 35 of the stimulable phosphor layer 45.

Figure 12:
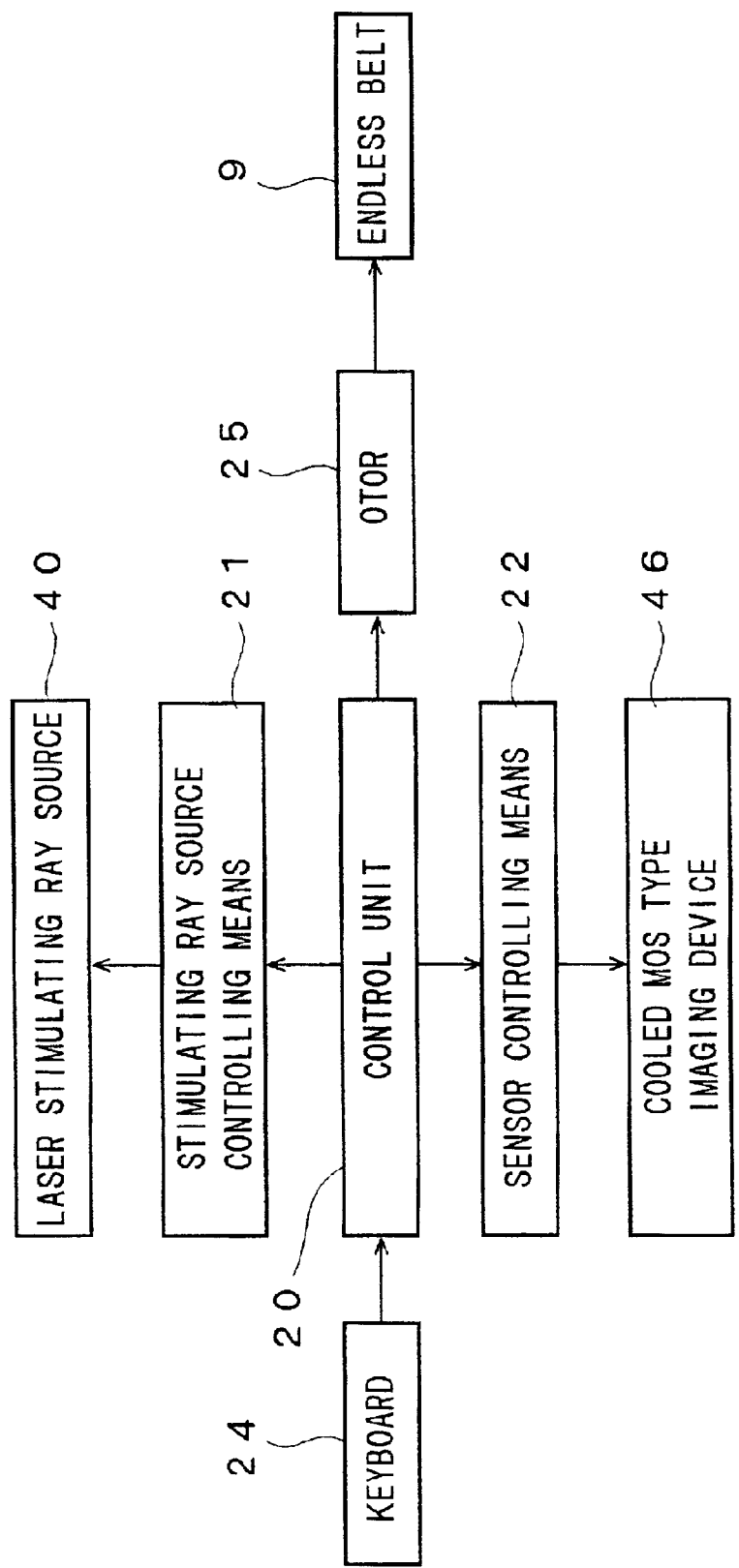
FIG. 12 is a block diagram of a control system, an input system and a drive system of an autoradiographic image reading apparatus which is a further preferred embodiment of the present invention.

FIG. 12 is a block diagram of a control system, an input system and a drive system of the autoradiographic image reading apparatus which is a further preferred embodiment of the present invention.

As shown in FIG. 12, in this embodiment, a cooled MOS type imaging device 46 provided with a cooling means (not shown) is employed instead of the cooled CCD linear sensor 8 according to the embodiment shown in FIGS. 1 to 8 and, therefore, the control system, the input system and the drive system of the fluorescent image reading apparatus according to this embodiment has the same configuration as that of the fluorescent image reading apparatus according the embodiment shown in FIG. 7 except that the stimulating ray source control means 21 is constituted so as to control the on-off operation of the laser stimulating ray source 40 and that the sensor controlling means 22 is constituted so as to control the on-off operation of the cooled MOS type imaging device 46.

In this embodiment, a stimulable phosphor sheet formed with a stimulable phosphor layer recording an autoradiographic image regarding locational information of a radioactive labeling substance is employed as an image carrier Locational information regarding a radioactive labeling substance is recorded in the stimulable phosphor layer formed on the stimulable sheet in the following manner. Locational information as termed here includes a variety of information relating to the location of radioactive labeled substances, or aggregations thereof, present in a specimen, such as the location, the shape, the concentration, the distribution or combinations thereof.

When locational information regarding a radioactive labeling substance, for example, in a gene obtained using a Southern blot-hybridization method is to be recorded in the stimulable phosphor layer formed on the stimulable sheet, first, a plurality of DNA fragments containing a specific gene are separated and distributed on a gel support medium by means of electrophoresis and are denatured by alkali processing to form single-stranded DNA.

Then, according to the known Southern blotting method, the gel support and a transfer support such as a nitrocellulose filter are stacked to transfer at least a part of the denatured DNA fragments onto the transfer support and the transferred DNA fragments are fixed on the transfer support by heating and irradiating with an ultraviolet beam.

Further, probes prepared by radioactively labeling DNA or RNA which is complementary to the DNA containing the specific gene and the denatured DNA fragments are hybridized by heating to form double-stranded DNA fragments or combined DNA and RNA. Since the denatured DNA fragments are fixed on the transfer support at this time, only the DNA fragments which are complimentary to the probe DNA or probe RNA are hybridized to acquire the radioactively labeled probe.

Then, the probes which have not formed hybrids are removed by washing with a proper solution and only the DNA fragments having a specific gene form hybrids with the radioactively labeled DNA or RNA on the transfer support to be radioactively labeled. The thus obtained transfer support is dried and the transfer support and the stimulable phosphor sheet are stacked for a certain period of time to expose the stimulable phosphor layer, and at least a part of the radiation emitted from the radioactively labeling substance on the transfer support is absorbed in the stimulable phosphor layer formed on the stimulable phosphor sheet, whereby the locational information regarding the radioactively labeled substance in the specimen is stored in the stimulable phosphor layer.

The thus constituted autoradiographic image reading apparatus according to this embodiment irradiates the stimulable phosphor layer 45 formed on the stimulable phosphor sheet 44 with a linear laser beam 43, photoelectrically detects residual stimulated emission to read an autoradiographic image of a radioactive labeling substance regarding locational information carried in the stimulable phosphor layer 45 and produces digital image data in the following manner.

The stimulable phosphor sheet 44 carrying an autoradiographic image of a radioactive labeling substance regarding locational information is first placed on the endless belt 9.

The kind of stimulable phosphor contained in the stimulable phosphor layer 45 is input by the user through the keyboard 24 together with a start signal.

The start signal and the kind of stimulable phosphor input through the keyboard 24 is input to the control unit 20 and when the control unit 20 receives the start signal, it outputs a drive signal to the motor 25 to cause it to drive the endless belt 9 until the stimulable phosphor sheet 44 placed on the endless belt 9 reaches a position where it can be irradiated with the laser beam 43.

At the same time, the control unit 20 accesses the table in which light emitting amount data and decay times of residual stimulated emission for each kind of stimulable phosphor are written, reads light emitting amount data and the decay time TT of residual stimulated emission of the input stimulable phosphor and stores them in a stimulation and detection control data memory (not shown).

The control unit 20 then determines, based on light emitting amount data of residual stimulated emission for the stimulable phosphor read out from the table and stored in the stimulation and detection control data memory, how many times the step of irradiation with the laser beam 43 and detection of residual stimulated emission should be repeated and stores the number p of repetition (p is an integer equal to or greater than 1) in the stimulation and detection control data memory.

At the same time, based on the read out decay time TT of residual fluorescence emission of the stimulable phosphor, the control unit 20 determines the time period TT1 during which the laser stimulating ray source 40 is held on and the stimulable phosphor is stimulated by the laser beam 43, the time tssi when the laser stimulating ray source 40 is turned on and the time tsei when the laser stimulating ray source 40 is turned off and further determines the time period TT2 during which the cooled MOS type imaging device 46 is held on and stimulated emission released from the stimulable phosphor is detected by the cooled MOS type imaging device 46, the time tdsi when the cooled MOS type imaging device 46 is turned on and the time tdei when the cooled MOS type imaging device 46 is turned off. The control unit 20 then stores the determined values in the stimulation and detection control data memory and outputs a stimulating ray irradiation start signal to the stimulating ray source control means 21.

Here, i designates the ith step of irradiation with the laser beam 43 and detection of residual stimulated emission.

FIG. 13 is a graph showing the relationship between irradiation time with the laser beam 43 and the intensity of stimulated emission released from a stimulable phosphor.

As a result, as shown in FIG. 13, the laser stimulating ray source 40 is turned on at the time tss1 and a laser beam 43 having a wavelength of 640 nm is emitted.

The laser beam 43 emitted from the laser stimulating ray source 40 enters the lens 41 and is diverged by the lens 41 in the direction indicated by the arrow Y in FIG. 11 and corresponding to the direction indicated by the arrow Y in FIG. 1 and is converged in a plane including the optical axis and the longitudinal axis of the lens 41 by the lens 41 in a direction perpendicular to the direction indicated by the arrow Y.

As a result, a linear laser beam 43 is generated and is linearly projected onto a stimulable phosphor layer 45 of the stimulable phosphor sheet 44 carrying an autoradiographic image, thereby simultaneously exciting all the stimulable phosphor contained in a linear area 35 of the stimulable phosphor layer 45.

Consequently, all stimulable phosphor contained in a linear area 35 of the stimulable phosphor layer 45 is simultaneously stimulated and stimulated emission is released. However, since the cooled MOS type imaging device 46 is held off while the laser stimulating ray source 40 is held on, stimulated emission is not detected by the cooled MOS type imaging device 46.

As shown in FIG. 13, at the time tse1 when the time period TT1 has passed after the laser stimulating ray source 40 was turned on, the control unit 20 outputs a stimulating ray irradiation stop signal to the stimulating ray source controlling means 21, thereby causing it to turn off the laser stimulating ray source 40.

Even after the laser stimulating ray source 40 has been turned off and the linear laser beam 43 is no longer emitted, stimulated emission called residual stimulated emission continues to be released from the stimulable phosphor contained in the stimulable phosphor layer 45.

As shown in FIG. 13, the control unit 20 outputs a light detection start signal to the sensor controlling means 22 at the time tds1, thereby causing it to turn on the cooled MOS type imaging device 46.

As a result, residual stimulated emission released from the stimulable phosphor contained in the stimulable phosphor layer 45 is condensed by the lens array 6 and enters the stimulating ray cut filter 7.

In this embodiment, a cut filter having a property of cutting a light component having a wavelength of 640 nm equal to that of the laser beam 43 and transmitting only a light component having a wavelength equal to that of stimulated emission is employed as a stimulating ray cut filter 7. Therefore, a light component having a wavelength of 640 nm equal to that of the laser beam 43 is cut by the stimulating ray cut filter 7 and only residual stimulated emission is transmitted through the stimulating ray cut filter 7 and enters the light receiving surface of the cooled MOS type imaging device 46 to form an image on the light receiving surface.

The cooled MOS type imaging device 46 receives light of the image thus formed on the light receiving surface and accumulates it in the form of electric charges therein.

As shown in FIG. 13, at the time tde1 when the time period TT2 has passed after the cooled MOS type imaging device 46 was turned on, the control unit 20 outputs a light detection stop signal to the sensor controlling means 22, thereby causing it to turn off the cooled MOS type imaging device 46.

Thus, the first step of irradiation with the laser beam 43 and detection of residual stimulated emission is completed.

Further, as shown in FIG. 13, a second step of irradiation with the laser beam 43 and detection of residual stimulated emission is started at the time tss2 and the control unit 20 outputs a stimulating ray irradiation start signal to the stimulating ray source controlling means 21, thereby again causing it to turn on the laser stimulating ray source 40.

As a result, the laser beam 43 having a wavelength of 640 nm is emitted from the laser stimulating ray source 40.

The laser beam 43 emitted from the laser stimulating ray source 40 enters the lens 41 and is diverged by the lens 41 in the direction indicated by the arrow Y in FIG. 11 and corresponding to the direction indicated by an arrow Y in FIG. 1 and is converged in a plane including the optical axis and the longitudinal axis of the lens 41 by the lens 41 in a direction perpendicular to the direction indicated by the arrow Y.

As a result, a linear laser beam 43 is generated and is linearly projected onto a stimulable phosphor layer 45 of the stimulable phosphor sheet 44 carrying an autoradiographic image, thereby simultaneously exciting all stimulable phosphor contained in a linear area 35 of the stimulable phosphor layer 45.

Consequently, all the stimulable phosphor contained in a linear area 35 of the stimulable phosphor layer 45 is simultaneously stimulated and stimulated emission is released. However, since the cooled MOS type imaging device 46 is held off while the laser stimulating ray source 40 is held on, stimulated emission is not detected by the cooled MOS type imaging device 46.

As shown in FIG. 13, at the time tse2 when the time period TT1 has passed after the laser stimulating ray source 40 was turned on, the control unit 20 outputs a stimulating ray irradiation stop signal to the stimulating ray source controlling means 21, thereby causing it to turn off the laser stimulating ray source 40.

As shown in FIG. 13, the control unit 20 then outputs a light detection start signal to the sensor controlling means 22 at the time tds2, thereby causing it to turn on the cooled MOS type imaging device 46.

As a result, residual stimulated emission released from the stimulable phosphor contained in the stimulable phosphor layer 45 after the completion of irradiation with the laser beam 43 is condensed by the lens array 6 and enters the stimulating ray cut filter 7.

Since the stimulating ray cut filter 7 has a property of cutting a light component having a wavelength of 640 nm equal to that of the laser beam 43 and transmitting only a light component having a wavelength equal to that of stimulated emission, a light component having a wavelength of 640 nm equal to that of the laser beam 43 is cut by the stimulating ray cut filter 7 and only residual stimulated emission is transmitted through the stimulating ray cut filter 7 and enters the light receiving surface of the cooled MOS type imaging device 46 to form an image on the light receiving surface.

The cooled MOS type imaging device 46 receives light of the image thus formed on the light receiving surface and accumulates it in the form of electric charges therein.

Thus, the second step of irradiation with the laser beam 43 and detection of residual stimulated emission is completed.

Similarly to the above, the step of irradiation with the laser beam 43 and detection of residual stimulated emission is repeated and when the number of the repeated steps becomes equal to the number p of repetition stored in the stimulation and detection control data memory, the control unit 20 causes an electric charge transfer means (not shown) to output analog image data accumulated in the form of electric charge by the cooled MOS type imaging device 46 to the amplifier 10 and causes the amplifier 10 to amplify the analog image data with a predetermined amplifying factor. The control unit 20 further causes the amplifier 10 to output amplified analog image data to the A/D converter 11, causes the A/D converter 11 to convert the analog image data to digital image data with a scale factor suitable for the signal fluctuation width and temporarily stores the digital image data in the image data buffer 12.

At the same time, the control unit 20 outputs a drive signal to the motor 25, thereby causing it to move the endless belt 9 by a distance equal to one scanning line in the direction indicated by the arrow Y in FIG. 1.

Similarly, an adjacent linear area of the stimulable phosphor layer 45 is irradiated with the laser beam 43 having a wavelength of 640 nm and emitted from the laser stimulating ray source 40 and a stimulable phosphor is stimulated. Residual stimulated emission released from the stimulable phosphor after the completion of irradiation with the laser beam 43 is received by the cooled MOS type imaging device 46 and accumulated in the form of electric charge therein.

Thus, when an pth step of irradiation with the laser beam 43 and detection of residual stimulated emission has been completed, the control unit 20 causes the electric charge transfer means (not shown) to output analog image data accumulated in the form of electric charge by the cooled MOS type imaging device 46 to the amplifier 10 and causes the amplifier 10 to amplify the analog image data with a predetermined amplifying factor. The control unit 20 further causes the amplifier 10 to output amplified analog image data to the AID converter 11, causes the A/D converter 11 to convert the analog image data to digital image data with a scale factor suitable for the signal fluctuation width and temporarily stores the digital image data in the image data buffer 12.

At the same time, the control unit 20 outputs a drive signal to the motor 25, thereby causing it to move the endless belt 9 by a distance equal to one scanning line in the direction indicated by the arrow Y in FIG. 1.

Thus, the whole surface of the stimulable phosphor layer 45 is scanned with the laser beam 43 having a wavelength of 640 nm and emitted from the laser stimulating ray source 40 and residual stimulated emission released from the stimulable phosphor is detected by the cooled MOS type imaging device 46 to produce analog image data. The analog image data are digitized by the AID converter 11 and an autoradiographic image regarding locational information of the radioactive labeling substance carried in the stimulable phosphor layer 45 is read. The thus produced digital image data are temporarily stored in the image data buffer 12.

When an autoradiographic image regarding locational information of the radioactive labeling substance carried in the stimulable phosphor layer 45 of one stimulable phosphor sheet 44 has been read, a data transfer signal is output from the control unit 20 to the image data buffer 12 and the digital image data temporarily stored in the image data buffer 12 are output to the image data storing means 13 and stored therein.

When the user requests production of a autoradiographic image by inputting an image producing signal through the keyboard 24, the control unit 20 outputs the digital image data stored in the image data storing means 13 to the image processing device 15.

The image processing device 15 effects necessary image processing on the thus input digital image data in accordance with the user's instructions and an autoradiographic image is displayed on the display means such as a CRT or a flat display panel such as a liquid crystal display, an organic EL display or the like based on the image processed digital image data.

According to this embodiment, although a linear area of the stimulable phosphor layer 45 formed on the stimulable phosphor sheet 44 is irradiated with the linear laser beam 43 having a wavelength of 640 nm and emitted from the laser stimulating ray source 40 and the stimulable phosphor contained in the stimulable phosphor layer 45 is stimulated, since the MOS type imaging device 46 is held off while the laser stimulating ray source 40 is held on, stimulated emission is not detected by the cooled MOS type imaging device 46. After the laser stimulating ray source 40 has been turned off, the MOS type imaging device 46 is turned on and residual stimulated emission released from the stimulable phosphor contained in the stimulable phosphor layer 45 after the completion of irradiation with the laser beam 43 is detected by the cooled MOS type imaging device 46. The analog image data produced by the cooled MOS type imaging device 46 are digitized by the A/D converter 11 to produce digital image data. Therefore, since the laser stimulating ray source 40 has been already turned off when the MOS type imaging device 46 detects residual stimulated emission, it is possible to prevent noise caused by detecting the laser beams 43 by the MOS type imaging device 46 from being generated in the digital image data and to improve an S/N ratio.

Further, according to this embodiment, since all the stimulable phosphor contained in a linear area of the stimulable phosphor layer 45 is simultaneously stimulated by irradiating the stimulable phosphor layer 45 formed on the stimulable phosphor sheet 44 with the linear laser beam 43 having a wavelength of 640 nm and emitted from the laser stimulating ray source 40, even if the step of irradiation with the laser beam 43 and detection of residual stimulated emission is repeated in order to increase the amount of residual stimulated emission to be received by the cooled MOS type imaging device 46, it is still possible to rapidly produce digital image data in which noise caused by photoelectrically detecting the laser beam 43 by the cooled MOS type imaging device 46 is lowered and which have a high S/N ratio.

Furthermore, according to this embodiment, since the autoradiographic image reading apparatus is provided with the stimulating ray cut filter 7 having a property of cutting a light component having a wavelength of the laser beam 43 emitted from the laser stimulating ray source 40 and transmitting only a light component having a wavelength of the stimulated emission, it is possible to produce digital image data in which noise caused by photoelectrically detecting the laser beam 43 by the cooled MOS type imaging device 46 is markedly lowered and which have a high SIN ratio.

The present invention has thus been shown and described with reference to specific embodiments. However, it should be noted that the present invention is in no way limited to the details of the described arrangements but changes and modifications may be made without departing from the scope of the appended claims.

For example, in the embodiment shown in FIG. 1 to 8, all the fluorescent dye contained in the linear area of the gel support 3 is stimulated by linearly irradiating the gel support 3 carrying an image of the fluorescent dye labeling the specimen with the laser beams 1 emitted from the plurality of laser diodes 2a, 2b, 2c, . . . constituting the laser diode array 2 and condensed by the cylindrical lens 4 in a single direction. However, instead of the laser diode array 2 constituted by the plurality of laser diodes 2a, 2b, 2c, . . . it is possible to employ a stimulating ray source for emitting a stimulating ray 33 of a center wavelength of 473 nm as in the embodiment shown in FIGS. 9 and 10 and linearly irradiate the gel support 3 with the line beam of a stimulating ray 33 transmitted through the slit 32 formed in the light blocking plate 31, thereby simultaneously stimulating all the fluorescent dye contained in the linear area of the gel support 3 and it is further possible to employ a laser stimulating ray source 40 for emitting a laser beam 43 having a wavelength of 473 nm as in the embodiment shown in FIGS. 11 and 12, generate a linear laser beam 43 by the lens 41 and linearly irradiate the gel support 3 therewith, thereby simultaneously stimulating all the fluorescent dye contained in the linear area of the gel support 3.

Further, in the embodiment shown in FIGS. 1 to 8, although the cooled CCD line sensor 8 constituted by arranging a plurality of sensor chips (photo-electrical elements) 16 in one line is used for detecting residual fluorescence emission 5, instead of the cooled CCD line sensor 8 constituted by the plurality of sensor chips 16, it is possible to employ a cooled photodiode array 36 as in the embodiment shown in FIGS. 9 and 10 and detect residual fluorescence emission and it is also possible to employ a cooled MOS type imaging device 46 as in the embodiment shown in FIGS. 11 and 12 and detect residual fluorescence emission. Moreover, it is possible to photoelectrically detect residual fluorescence emission using other types of solid state imaging devices.

Furthermore, in the embodiment shown in FIGS. 1 to 8, although residual fluorescence emission released from the fluorescent dye is detected using the cooled CCD line sensor 8 provided with a cooling means, residual fluorescence emission may be detected using a CCD line sensor which is not provided with any cooling means instead of the cooled CCD line sensor 8 provided with a cooling means.

Moreover, in the embodiment shown in FIGS. 1 to 8, although an image of the fluorescent dye carried in the gel support 3 is read, an image of a fluorescent substance such as a fluorescent dye carried in the membrane filter 34 as in the embodiment shown in FIGS. 9 and 10, an image of a fluorescent substance such as a fluorescent dye carried in a transfer support or an image of a fluorescent substance such as a fluorescent dye carried in a micro-array may be read. It is further possible to read an autoradiographic image regarding locational information of a radioactive labeling substance carried in a stimulable phosphor layer of a stimulable phosphor sheet as in the embodiment shown in FIGS. 11 and 12, an image of a radioactive labeling substance carried in a micro-array, a chemiluminescent image carried in a stimulable phosphor layer of a stimulable phosphor sheet, an electron microscopic image carried in a stimulable phosphor layer of a stimulable phosphor sheet, a radiographic diffraction image carried in a stimulable phosphor layer of a stimulable phosphor sheet and the like.

Furthermore, in the embodiment shown in FIGS. 9 and 10, all the fluorescent dye contained in the linear area of the membrane filter 34 is simultaneously stimulated by employing the stimulating ray source 30 for emitting a stimulating ray 33 having a center wavelength of 340 nm and linearly irradiating the membrane filter 34 with the line beam of the stimulating ray 33 transmitted through the slit 32 formed in the light blocking plate 31, instead of using the stimulating ray source 30 for emitting a stimulating ray 33 having a wavelength of 340 nm and the light blocking plate 31 formed with the slit 32, all the fluorescent dye contained in the linear area of the membrane filter 34 may be simultaneously stimulated by linearly irradiating the membrane filter 34 carrying an image of the fluorescent dye labeling the specimen with the linear laser beam 1 emitted from the plurality of laser diodes 2a, 2b, 2c, . . . constituting the laser diode array 2 and condensed by the cylindrical lens 4 in a single direction as in the embodiment shown in FIGS. 1 to 8 or all the fluorescent dye contained in the linear area of the membrane filter 34 may be simultaneously stimulated by using the laser stimulating ray source 40 for emitting a laser beam having a wavelength of 340 nm as in the embodiment shown in FIGS. 11 and 12 and linearly irradiating the membrane filter 34 with a linearly laser beam 43 produced by the lens 41.

Moreover, in the embodiment shown in FIGS. 9 and 10, although the cooled photodiode array 36 is used for detecting residual fluorescence emission, residual fluorescence emission may be detected using a cooled CCD line sensor 8 constituted by arranging a plurality of sensor chips (photoelectrical elements) 16 in a single line as in the embodiment shown in FIGS. 1 to 8 or residual fluorescence emission may be detected using a cooled MOS type imaging device 46 as in the embodiment shown in FIGS. 11 and 12. Further, other types of solid state imaging devices may be used for photoelectrically detecting residual fluorescence emission.

Furthermore, in the embodiment shown in FIGS. 9 and 10, although the cooled photodiode array 36 provided with the cooling means is used for detecting residual fluorescence emission, residual fluorescence emission may be detected using a photodiode array which is not provided with any cooling means instead of the cooled photodiode array 36 provided with the cooling means.

Moreover, in the embodiment shown in FIGS. 9 and 10, although an image of the fluorescent dye carried in the membrane filter 34 is read, an image of a fluorescent substance such as a fluorescent dye carried in the gel support 3 as in the embodiment shown in FIGS. 1 to 8, an image of a fluorescent substance such as a fluorescent dye carried in a transfer support or an image of a fluorescent substance such as a fluorescent dye carried in a micro-array may be read. It is further possible to read an autoradiographic image regarding locational information of a radioactive labeling substance carried in a stimulable phosphor layer of a stimulable phosphor sheet as in the embodiment shown in FIGS. 11 and 12, an image of a radioactive labeling substance carried in a micro-array, a chemiluminescent image carried in a stimulable phosphor layer of a stimulable phosphor sheet, an electron microscopic image carried in a stimulable phosphor layer of a stimulable phosphor sheet, a radiographic diffraction image carried in a stimulable phosphor layer of a stimulable phosphor sheet and the like.

Furthermore, in the embodiment shown in FIGS. 11 and 12, the laser stimulating ray source 40 for emitting a laser beam 43 having a wavelength of 640 nm is employed and the stimulable phosphor layer 45 formed on the stimulable phosphor sheet 44 is linearly irradiated with the linear laser beam 43 produced by the lens 41, thereby simultaneously exciting all the stimulable phosphor contained in the linear area of the stimulable phosphor layer 45. However, instead of using the laser stimulating ray source 40 for emitting a laser beam 43 having a wavelength of 640 nm and the lens 41, all the stimulable phosphor contained in the linear area of the stimulable phosphor layer 45 may be simultaneously stimulated by employing a laser diode array 2 constituted by a plurality of laser diodes 2a, 2b, 2c, . . . as in the embodiment shown in FIGS. 1 to 8 and linearly irradiating the stimulable phosphor layer 45 formed on the stimulable phosphor sheet 44 with a linear laser beam 1 emitted from the plurality of laser diodes 2a, 2b, 2c, . . . and condensed by the cylindrical lens 4 in a single direction or all the stimulable phosphor contained in the linear area of the stimulable phosphor layer 45 may be simultaneously stimulated by employing a stimulating ray source 30 for emitting a stimulating ray 33 having a center wavelength of 640 nm and a light blocking plate 31 formed with a slit 32 as in the embodiment shown in FIGS. 9 and 10 and linearly irradiating the stimulable phosphor layer 45 with a line beam of the stimulating ray transmitted through the slit 32 formed in the light blocking plate 31.

Moreover, in the embodiment shown in FIGS. 11 and 12, although the cooled MOS type imaging device 46 is used for detecting residual stimulated emission, instead of the cooled MOS type imaging device 46, it is possible to detect residual stimulated emission using a cooled CCD line sensor 8 constituted by arranging a plurality of sensor chips (photoelectrical elements) 16 in a single line as in the embodiment shown in FIGS. 1 to 8 or using a cooled photodiode array 36 as in the embodiment shown in FIGS. 9 and 10. Further, residual stimulated emission may be photoelectrically detected using other types of solid state imaging devices.

Furthermore, in the embodiment shown in FIGS. 11 and 12, although the cooled MOS type imaging device 46 provided with the cooling means is used for detecting residual stimulated emission, residual stimulated emission may be detected using a MOS type imaging device provided with no cooling means instead of the cooled MOS type imaging device 46 provided with the cooling means.

Moreover, in the above described embodiments, although the stimulating ray cut filter 7 for cutting a light component having a wavelength of a stimulating ray is used, if the photoelectrical detection of residual fluorescence emission or residual stimulated emission is started when a time period sufficiently for enabling a stimulating ray to be isolated has passed after the completion of irradiation with the stimulating ray, the stimulating ray cut filter 7 may be omitted.

Further, in the above described embodiments, although a single stimulating ray source 2, 30, 40 is provided, two or more stimulating ray sources for emitting stimulating rays having different wavelengths from each other may be provided and selectively used depending upon the kind of a labeling substance if the stimulating rays emitted from the stimulating ray sources are led to the lens 41 using a light guide means such as an optical fiber.

Furthermore, in the embodiment shown in FIGS. 11 and 12, an autoradiographic image regarding locational information of the radioactive labeling substance is read. However, the image reading apparatus shown in FIGS. 11 and 12 is not limited to be used for reading such an image but can be used for reading an image of a radioactive labeling substance carried in a micro-array, a chemiluinescent image carried in a stimulable phosphor layer of a stimulable phosphor sheet, an electron microscopic image carried in a stimulable phosphor layer of a stimulable phosphor sheet, a radiographic diffraction image carried in a stimulable phosphor layer of a stimulable phosphor sheet and like. Further, the image reading apparatus shown in FIGS. 11 and 12 can be used for reading an image of a fluorescent substance such as a fluorescent dye carried in a gel support 3 as in the embodiment shown in FIGS. 1 to 8, an image of a fluorescent substance such as a fluorescent dye carried in a membrane filter 34 as in the embodiment shown in FIGS. 9 and 10 and an image of a fluorescent substance such as a fluorescent dye carried in a transfer support, a micro-array or the like.

Moreover, the laser diode array 2 constituted by the plurality of laser diodes 2a, 2b, 2c, . . . is used in the embodiment shown in FIGS. 1 to 8 and the laser stimulating ray source 40 is used in the embodiment shown in FIGS. 11 and 12. However, a stimulating ray may be linearly projected onto an image carrier such as a gel support 3 using an LED array instead of the laser diode array 2 in the embodiment shown in FIGS. 1 to 8 and a stimulating ray may be linearly projected onto an image carrier such as a stimulable phosphor sheet 44 using an LED stimulating ray source instead of the laser stimulating ray source 40 in the embodiment shown in FIGS. 11 and 12.

Further, in the embodiment shown in FIGS. 9 and 10, although a line beam of a stimulating ray 33 is generated using the LED stimulating ray source 30 and the light blocking plate 31 formed with the slit 32 and is linearly projected onto an image carrier such as a membrane filter 34, a line beam of a stimulating ray 33 may be generated using a lamp for emitting a stimulating ray, instead of the LED stimulating ray source 30, and the light blocking plate 31 formed with the slit 32 and be linearly projected onto an image carrier such as a membrane filter 34.

Furthermore, SYPRO Ruby (registered trademark) is used as a fluorescent dye in the embodiment shown in FIGS. 1 to 8 and DELFIA (registered trademark) is used as a fluorescent dye in the embodiment shown in FIGS. 9 and 10. However, any fluorescent dye or fluorescent substance capable of releasing residual fluorescence emission whose decay time is longer than a predetermined length may be used and the fluorescent dye or fluorescent substance is not limited to SYPRO Ruby (registered trademark) or DELFIA (registered trademark).

Moreover, in the above described embodiments, the linear laser beam 1, the line beam of the stimulating ray 33 or the linear laser beam 43 is held stationary while the gel support 3, the membrane filter 34 or the stimulable phosphor sheet 44 is moved together with the endless belt 9, whereby the surface of the gel support 3, the membrane filter 34 or the stimulable phosphor sheet 44 is scanned with the linear laser beam 1, the line beam of the stimulating ray 33 or the linear laser beam 43. However, it is possible to hold the gel support 3, the membrane filter 34 or the stimulable phosphor sheet 44 stationary and move the linear laser beam 1, the line beam of the stimulating ray 33 or the linear laser beam 43 in a direction perpendicular to the longitudinal direction of the linear laser beam 1, the line beam of the stimulating ray 33 or the linear laser beam 43, thereby scanning the surface of the gel support 3, the membrane filter 34 or the stimulable phosphor sheet 44 with the linear laser beam 1, the line beam of the stimulating ray 33 or the linear laser beam 43.

Further, in the present invention, the respective means need not necessarily be physical means and arrangements whereby the functions of the respective means are accomplished by software fall within the scope of the present invention. In addition, the function of a single means may be accomplished by two or more physical means and the functions of two or more means may be accomplished by a single physical means.

According to the present invention, it is possible to provide an image reading method and apparatus which can produce low noise image data rapidly and with a simple operation by irradiating an image carrier including two-dimensionally distributed spots of a labeling substance such as a fluorescent substance, a radioactive labeling substance or the like with a stimulating ray to excite the labeling substance and photoelectrically detecting light released from the labeling substance.

What is claimed is:

1. An image reading method for producing image data by irradiating an image carrier including two-dimensionally distributed spots of a labeling substance with a stimulating ray to excite the labeling substance and photoelectrically detecting light released from the labeling substance, the image reading method further comprising a stimulation and detection step of irradiating the image carrier with a line beam of the stimulating ray to excite the labeling substance and photoelectrically detecting light released from the labeling substance after the completion of irradiation with the stimulating ray.

2. An image reading method in accordance with claim 1 wherein the image carrier is intermittently moved relative to the line beam of the stimulating ray in a direction perpendicular to a longitudinal direction of the line beam and the stimulation and detection step is performed each time the image carrier is moved, thereby scanning the whole surface of the image carrier with the line beam of the stimulating ray and image data are produced by photoelectrically detecting light released from the labeling substance contained in the spots two-dimensionally distributed in the image carrier.

3. An image reading method in accordance with claim 1, wherein the stimulation and detection step is repeated two or more times.

4. An image reading method in accordance with claim 1, wherein the line beam of the stimulating ray is emitted from a laser diode array or a laser diode array constituted by one or more laser diodes.

5. An image reading method in accordance with claim 1, wherein a laser beam emitted from a laser stimulating ray source is shaped using a lens to produce the line beam of the stimulating ray.

6. An image reading method in accordance with claim 1, wherein the line beam of the stimulating ray is emitted from an LED array constituted by one or more LEDs.

7. An image reading method in accordance with claim 1, wherein a stimulating ray emitted from an LED stimulating ray source is shaped using a lens to produce the line beam of the stimulating ray.

8. An image reading method in accordance with claim 1, wherein a stimulating ray emitted from an LED stimulating ray source is shaped by a slit to produce the line beam of the stimulating ray.

9. An image reading method in accordance with claim 1, wherein light released from the labeling substance is photoelectrically detected using a solid state imaging device.

10. An image reading method in accordance with claim 9, wherein light released from the labeling substance is photoelectrically detected using a CCD line sensor.

11. An image reading method in accordance with claim 10, wherein light released from the labeling substance is photoelectrically detected using a cooled CCD line sensor.

12. An image reading method in accordance with claim 9, wherein light released from the labeling substance is photoelectrically detected using a photodiode array.

13. An image reading method in accordance with claim 12, wherein light released from the labeling substance is photoelectrically detected using a cooled photodiode array.

14. An image reading method in accordance with claim 9, wherein light released from the labeling substance is photoelectrically detected using a MOS type imaging device.

15. An image reading method in accordance with claim 14, wherein light released from the labeling substance is photoelectrically detected using a cooled MOS type imaging device.

16. An image reading method in accordance with claim 1, wherein the labeling substance is formed of a fluorescent substance.

17. An image reading method in accordance with claim 16, wherein the image carrier is constituted as a membrane filter including the fluorescent substance contained in two-dimensionally distributed spots.

18. An image reading method in accordance with claim 16, wherein the image carrier is constituted as a gel support including the fluorescent substance contained in two-dimensionally distributed spots.

19. An image reading method in accordance with claim 16, wherein the image carrier is constituted as a micro-array including the fluorescent substance contained in two-dimensionally distributed spots.

20. An image reading method in accordance with claim 1, wherein the image carrier is constituted as a stimulable phosphor sheet formed with a stimulable phosphor layer including a radioactive labeling substance contained in two-dimensionally distributed spots.

21. An image reading apparatus adapted for irradiating an image carrier including a labeling substance contained in two-dimensionally distributed spots with a stimulating ray and photoelectrically detecting light released from the labeling substance, thereby producing image data, the image reading apparatus comprising at least one stimulating ray source for emitting a stimulating ray, a stimulating ray shaping means for shaping the stimulating ray emitted from the at least one stimulating ray source into a line beam, a sensor for photoelectrically detecting light released from the labeling substance, and a control means for performing a stimulation and detection step of irradiating the image carrier including the labeling substance contained in the two-dimensionally distributed spots with the line beam of the stimulating ray to stimulate the labeling substance, stopping irradiation with the line beam of the stimulating ray and causing the sensor to photoelectrically detect light released from the labeling substance after the completion of irradiation with the line beam of the stimulating ray.

22. An image reading apparatus in accordance with claim 21, which further comprises a scanning means for intermittently moving the image carrier relative to the line beam of the stimulating ray in a direction perpendicular to a longitudinal direction of the line beam and wherein the control means is constituted so as to perform the stimulation and detection step each time the image carrier is intermittently moved by the scanning means, thereby scanning a whole surface of the image carrier with the line beam of the stimulating ray and the sensor is constituted so as to photoelectrically detect light released from the labeling substance contained in the spots two-dimensionally distributed in the image carrier to produce image data.

23. An image reading apparatus in accordance with claim 21, wherein the control means is constituted so as to repeat the stimulation and detection step two or more times.

24. An image reading apparatus in accordance with claim 21, wherein the at least one stimulating ray source and the stimulating ray shaping means are constituted as a laser diode array or a laser diode array provided with two or more laser diodes.

25. An image reading apparatus in accordance with claim 21, wherein the at least one stimulating ray source is constituted as a laser stimulating ray source and the stimulating ray shaping means is constituted as a lens.

26. An image reading apparatus in accordance with claim 21, wherein the at least one stimulating ray source and the stimulating ray shaping means are constituted as an LED array provided with one or more LEDs.

27. An image reading apparatus in accordance with claim 21, wherein the at least one stimulating ray source is constituted as an LED stimulating ray source and the stimulating ray shaping means is constituted as a lens.

28. An image reading apparatus in accordance with claim 21, wherein the stimulating ray shaping means is constituted as a slit.

29. An image reading apparatus in accordance with claim 21 wherein the sensor is constituted as a solid state imaging device.

30. An image reading apparatus in accordance with claim 29, wherein the sensor is constituted as a CCD line sensor.

31. An image reading apparatus in accordance with claim 29, wherein the sensor is constituted as a cooled CCD line sensor.

32. An image reading apparatus in accordance with claim 29, wherein the sensor is constituted as a photodiode array.

33. An image reading apparatus in accordance with claim 32, wherein the sensor is constituted as a cooled photodiode array.

34. An image reading apparatus in accordance with claim 29, wherein the sensor is constituted as a MOS type imaging device.

35. An image reading apparatus in accordance with claim 29, wherein the sensor is constituted as a cooled MOS type imaging device.

36. An image reading apparatus in accordance with claim 21, which further comprises a stimulating ray cut filter disposed in a path of light released from the labeling substance for cutting at least a light component having a wavelength of the stimulating ray.

37. An image reading apparatus in accordance with claim 21, wherein the labeling substance is formed of a fluorescent substance.

38. An image reading apparatus in accordance with claim 37, wherein the image carrier is constituted as a membrane filter including the fluorescent substance contained in two-dimensionally distributed spots.

39. An image reading apparatus in accordance with claim 37, wherein the image carrier is constituted as a gel support including the fluorescent substance contained in two-dimensionally distributed spots.

40. An image reading apparatus in accordance with claim 37, wherein the image carrier is constituted as a micro-array including the fluorescent substance contained in two-dimensionally distributed spots.

41. An image reading apparatus in accordance with claim 21, wherein the image carrier is constituted as a stimulable phosphor sheet formed with a stimulable phosphor layer including a radioactive labeling substance contained in two-dimensionally distributed spots.

* * * * *